US009710968B2

(12) United States Patent
Dillavou et al.

(10) Patent No.: US 9,710,968 B2
(45) Date of Patent: Jul. 18, 2017

(54) SYSTEM AND METHOD FOR ROLE-SWITCHING IN MULTI-REALITY ENVIRONMENTS

(71) Applicant: VIPAAR, LLC, Birmingham, AL (US)

(72) Inventors: Marcus W. Dillavou, Birmingham, AL (US); Drew Steven Deaton, Birmingham, AL (US); Matthew Benton May, Birmingham, AL (US)

(73) Assignee: HELP LIGHTNING, INC., Birmingham, AL (US)

( * ) Notice: Subject to any disclaimer, the term of this patent is extended or adjusted under 35 U.S.C. 154(b) by 144 days.

(21) Appl. No.: 13/727,202

(22) Filed: Dec. 26, 2012

(65) Prior Publication Data
US 2014/0176533 A1 Jun. 26, 2014

(51) Int. Cl.
G09G 5/00 (2006.01)
G06T 19/00 (2011.01)
A63F 13/65 (2014.01)

(52) U.S. Cl.
CPC ............ G06T 19/006 (2013.01); A63F 13/65 (2014.09); *G06T 2219/024* (2013.01)

(58) Field of Classification Search
CPC ............................. G06T 19/006; G06T 19/00
USPC ........................................................ 345/633
See application file for complete search history.

(56) References Cited

U.S. PATENT DOCUMENTS

| 3,931,679 A | 1/1976 | Carter |
| 4,601,664 A | 7/1986 | Bertino, III et al. |
| 4,970,666 A | 11/1990 | Welsh et al. |
| 5,102,340 A | 4/1992 | Berlinghoff et al. |
| 5,391,081 A | 2/1995 | Lampotang et al. |
| 5,403,192 A | 4/1995 | Kleinwaks et al. |
| 5,584,701 A | 12/1996 | Lampotang et al. |
| 5,769,641 A | 6/1998 | Lampotang et al. |
| 5,772,442 A | 6/1998 | Lampotang et al. |
| 5,779,484 A | 7/1998 | Lampotang et al. |
| 5,853,292 A | 12/1998 | Eggert et al. |
| 5,868,579 A | 2/1999 | Lampotang et al. |
| 5,882,207 A | 3/1999 | Lampotang et al. |
| 5,890,908 A | 4/1999 | Lampotang et al. |
| 5,900,923 A | 5/1999 | Prendergast et al. |
| 5,941,710 A | 8/1999 | Lampotang et al. |

(Continued)

FOREIGN PATENT DOCUMENTS

| AU | 2008270883 A1 | 1/2009 |
| AU | 2012295324 | 8/2012 |

(Continued)

OTHER PUBLICATIONS

U.S. Appl. No. 13/929,080, filed Jun. 27, 2013, Dillavou (Vipaar, LLC).

(Continued)

*Primary Examiner* — Jin Ge
(74) *Attorney, Agent, or Firm* — Baker & Hostetler LLP

(57) ABSTRACT

Provided herein are methods and systems for role designation with multiple sources. A method for role designation can comprise rendering a common field of interest that reflects a presence of a plurality of elements, wherein at least one of the elements is a remote element located remotely from another of the elements, receiving a role designation, and updating the common field of interest based upon the role designation.

20 Claims, 22 Drawing Sheets

(56) References Cited

U.S. PATENT DOCUMENTS

| | | |
|---|---|---|
| 6,042,477 A | 3/2000 | Addink |
| 6,157,677 A | 12/2000 | Martens et al. |
| 6,166,744 A | 12/2000 | Jaszlics et al. |
| 6,193,519 B1 | 2/2001 | Eggert et al. |
| 6,220,866 B1 | 4/2001 | Amend et al. |
| 6,241,609 B1 | 6/2001 | Rutgers |
| 6,246,975 B1 | 6/2001 | Rivonelli et al. |
| 6,257,234 B1 | 7/2001 | Sun |
| 6,273,728 B1 | 8/2001 | van Meurs et al. |
| 6,301,339 B1 | 10/2001 | Staples et al. |
| 6,317,165 B1 | 11/2001 | Balram et al. |
| 6,443,735 B1 | 9/2002 | Eggert et al. |
| 6,461,165 B1 | 10/2002 | Takashina et al. |
| 6,503,087 B1 | 1/2003 | Eggert et al. |
| 6,527,558 B1 | 3/2003 | Eggert et al. |
| 6,535,714 B2 | 3/2003 | Melker et al. |
| 6,570,563 B1* | 5/2003 | Honda .................. 345/419 |
| 6,608,628 B1 | 8/2003 | Ross et al. |
| 6,692,258 B1 | 2/2004 | Kurzweil et al. |
| 6,697,451 B2 | 2/2004 | Acharya et al. |
| 6,747,672 B1 | 6/2004 | Haakonsen et al. |
| 6,758,676 B2 | 7/2004 | Eggert et al. |
| 6,774,885 B1 | 8/2004 | Even-Zohar |
| 6,780,016 B1 | 8/2004 | Toly |
| 6,921,267 B2 | 7/2005 | van Oostrom et al. |
| 7,015,954 B1 | 3/2006 | Foote et al. |
| 7,181,690 B1* | 2/2007 | Leahy et al. ............. 715/706 |
| 7,259,761 B2 | 8/2007 | Shih et al. |
| 7,367,809 B2 | 5/2008 | Takahashi |
| 7,373,377 B2 | 5/2008 | Altieri |
| 7,376,903 B2 | 5/2008 | Morita et al. |
| 7,403,664 B2 | 7/2008 | Porikli et al. |
| 7,728,868 B2 | 6/2010 | Razzaque et al. |
| 7,787,927 B2 | 8/2010 | Wood et al. |
| 7,949,616 B2 | 5/2011 | Levy et al. |
| 8,046,408 B2 | 10/2011 | Torabi |
| 8,179,412 B2 | 5/2012 | Swanson |
| 8,336,777 B1 | 12/2012 | Pantuso et al. |
| 8,398,541 B2 | 3/2013 | DiMaio et al. |
| 8,520,024 B2 | 8/2013 | Guthrie |
| 2001/0026630 A1 | 10/2001 | Honda |
| 2004/0009459 A1 | 1/2004 | Anderson et al. |
| 2004/0091845 A1 | 5/2004 | Azerad et al. |
| 2004/0161731 A1 | 8/2004 | Arington et al. |
| 2004/0189701 A1 | 9/2004 | Badt |
| 2004/0193441 A1 | 9/2004 | Altieri |
| 2004/0260170 A1 | 12/2004 | Wood et al. |
| 2005/0197818 A1 | 9/2005 | Monfared et al. |
| 2005/0203367 A1 | 9/2005 | Ahmed et al. |
| 2005/0203380 A1 | 9/2005 | Sauer et al. |
| 2005/0267778 A1 | 12/2005 | Kazman |
| 2005/0273185 A1 | 12/2005 | Teiwes et al. |
| 2005/0289472 A1 | 12/2005 | Morita et al. |
| 2006/0187224 A1 | 8/2006 | Ehrlich |
| 2007/0018975 A1 | 1/2007 | Chuanggui et al. |
| 2007/0048702 A1 | 3/2007 | Jang et al. |
| 2007/0055578 A1 | 3/2007 | Ashton |
| 2007/0064098 A1 | 3/2007 | Tran |
| 2007/0149290 A1 | 6/2007 | Nickell et al. |
| 2007/0248261 A1 | 10/2007 | Zhou et al. |
| 2008/0024594 A1 | 1/2008 | Ritchey |
| 2008/0025640 A1 | 1/2008 | Trudeau et al. |
| 2008/0079752 A1 | 4/2008 | Gates et al. |
| 2008/0123910 A1 | 5/2008 | Zhu |
| 2008/0123927 A1 | 5/2008 | Miga et al. |
| 2008/0231626 A1* | 9/2008 | Mohamed et al. .......... 345/418 |
| 2008/0278633 A1 | 11/2008 | Tsoupko-Sitnikov et al. |
| 2009/0058987 A1 | 3/2009 | Thielman et al. |
| 2009/0287089 A1 | 11/2009 | Spector |
| 2009/0300122 A1 | 12/2009 | Freer |
| 2010/0141555 A1 | 6/2010 | Rorberg et al. |
| 2010/0295921 A1* | 11/2010 | Guthrie et al. ............ 348/14.08 |
| 2010/0315418 A1 | 12/2010 | Woo |
| 2011/0018959 A1 | 1/2011 | Friel et al. |
| 2011/0084983 A1 | 4/2011 | Demaine |
| 2011/0188744 A1* | 8/2011 | Sun ............................. 382/162 |
| 2011/0216060 A1* | 9/2011 | Weising et al. ............. 345/419 |
| 2011/0270135 A1 | 11/2011 | Dooley et al. |
| 2012/0201456 A1* | 8/2012 | El-Mahdy et al. .......... 382/167 |
| 2012/0320157 A1* | 12/2012 | Junuzovic et al. ............ 348/46 |
| 2013/0038632 A1* | 2/2013 | Dillavou et al. ............. 345/633 |
| 2013/0308827 A1 | 11/2013 | Dillavou |
| 2014/0176533 A1 | 6/2014 | Dillavou |

FOREIGN PATENT DOCUMENTS

| | | |
|---|---|---|
| AU | 2008270883 | 5/2013 |
| AU | 2012295324 A1 | 3/2014 |
| CA | 2694095 | 5/2008 |
| CA | 2694095 A1 | 1/2009 |
| CN | 200880024323.7 | 5/2008 |
| CN | 101743567 | 1/2009 |
| CN | 201280048083.0 | 8/2012 |
| CN | 201280048083.0 | 2/2013 |
| EP | 1804209 A1 | 7/2007 |
| EP | 8826034.4 | 5/2008 |
| EP | 8826034.4 | 1/2009 |
| EP | 2163092 A2 | 3/2010 |
| EP | 12824190.8 | 8/2012 |
| EP | 2742461 A1 | 6/2014 |
| HK | 114460 | 1/2009 |
| HK | 10111098.6 | 11/2010 |
| IN | 7420/CHENP/2009 | 5/2008 |
| IN | 7420/CHENP/2009 | 1/2009 |
| JP | 05227463 A | 9/1993 |
| JP | 2002074370 A | 3/2002 |
| JP | 2007535875 A | 12/2007 |
| JP | 2010-508631 | 5/2008 |
| JP | 2013-24298 | 1/2009 |
| JP | 2009134693 A | 6/2009 |
| JP | 2010-528354 A | 8/2010 |
| JP | 2013-24298 | 2/2013 |
| NZ | 582133 | 5/2008 |
| NZ | 621149 | 8/2012 |
| NZ | 582133 A | 12/2012 |
| NZ | 621149 | 2/2013 |
| WO | WO-96/09722 A1 | 3/1996 |
| WO | WO-00/49475 A2 | 8/2000 |
| WO | WO-2005/119554 A2 | 12/2005 |
| WO | WO-2006/108279 A1 | 10/2006 |
| WO | WO-2007/059477 A2 | 5/2007 |
| WO | PCT/US2008/064118 | 5/2008 |
| WO | WO-2009/005901 A2 | 1/2009 |
| WO | PCT/US2012/050238 | 8/2012 |
| WO | WO-2013/025457 A1 | 2/2013 |
| WO | PCT/US2013/041967 | 5/2013 |
| WO | WO-2013/177125 A2 | 11/2013 |
| WO | PCT/US2013/077824 | 12/2013 |
| WO | WO-2014/105961 A1 | 7/2014 |

OTHER PUBLICATIONS

U.S. Appl. No. 60/930,874, filed May 18, 2007, Guthrie (UAB Research Foundation).

U.S. Appl. No. 13/929,080, Dillavou.

U.S. Appl. No. 60/930,874, Guthrie.

Danglemaier, et al. "Virtual and augmented reality support for discrete manufacturing system simulation," Computers in Industry, vol. 56, pp. 371-383 (2005).

Gibson, et al. "Simulating surgery using volumetric object representations, real-time volume rendering and haptic feedback," Mitsubishi Research Laboratories, pp. 1-21 (1997).

Hamza-Lup, F.G., "A distrubuted augmented reality system for medical training and simulation," Artcile Retrieved from the Internet. <URL: http://web.archive.org/web/20070416201920/http://www.cs.ucf.edu/-ceh/Publications/Papers/Content/Link04Hamza-LupRollandHughes.pdf> pp. 1-18, (2008).

International Search Report issued Apr. 15, 2014 for International Patent Application No. PCT/US2013/077824, which was filed on Dec. 26, 2013 and published as WO 2014/105961 on Jul. 3, 2014 (Inventor—Dillavou; Applicant—Vipaar, LLC) (pp. 1-2).

(56) References Cited

OTHER PUBLICATIONS

Ai, et al. "Tele-immersive medical educational environment," University of Illinois at Chicago. VRMedLab, School of Biomedical and Health Information Sciences, pp. 1-7, 2002.
Akatsuka, et al. Compensation for end to end delays in a vr system,: Proceedings of IEEE Virtual Reality Annual International Symposium, pp. 156-159 (1998).
Ballantyne, et al. "The da vinci telerobotic surgical systems: the virtual operative field and telepresence surgery," Surg Clin North Am., vol. 83(6), pp. 1293-1304 (2003).
Billinghurst, et al. "Mixing realities in shared space: an augmented reality interface for collarborative computing," Multimedia and Expo, vol. 3, pp. 1641-1644 (2000).
Billinghurst, et al. "Real world teleconferencing," IEEE Computer Graphics, vol. 22(6), pp. 11-13 (2002).
Birkfellner, et al. "Computer-enhanced stereoscopic vision in a head-mounted operating binocular," Phys Med Biol, vol. 48(3), pp. N49-N57 (2003).
Haluck, et al. Reliability and validity of endotower, a virtual reality trainer for angled endoscope navigation, J.D. Westwood, et al. (Eds), Medicine Meets Virtual Reality, IOS Press, pp. 1-6 (2002).
Kurosaki, et al. "Skill transmission for hand positioning task through view-sharing system," Graduate School of Information Science and Technology, Osaka University, pp. 1-4.
Nicolau, et al. "An augmented reality system to guide radio-frequency tumour ablation," Computer Animation and Virtual World (previously the Journal of Visualization & Computer Animation, vol. 16(1), pp. 1-10, 200 (2004).
Nishikawa, et al. "Mutual view sharing system for real-time telecommunication," Systems and Computers in Japan, vol. 37(14), pp. 292-304 (2006).
Paul, et al. "Augmented virtuality based on stereoscopic reconstruction in multimodal image-guided neurosurgery: methods and performance evaluation," IEEE Trans Med Imaging, vol. 24(11), pp. 1500-1511 (2005).
Satava, R.M., "Medical applications of virtual reality," J. Med Systems, vol. 19, pp. 275-280 (1996).
Shuhaiber, J.H., "Augmented reality in surgery," Arch Surg., vol. 139(2), pp. 170-174 (2004).
So, et al. "Experimental studies of the use of phase lead filters to compensate lags," IEEE Transactions on Systems, Man, and Cybernetics—Part A: Systems and Humans, vol. 26, No. 4, pp. 445-454 (1996).
Soler, et al. "Virtual reality, augmented reality and robotics in surgical procedures of the liver," Th. M. Buzug and T.C. Lueth, editors. Perspectives in Image-guided Surgery, pp. 476-484 (2004).
Stafford, et al. "User evaluation of God-like interaction techniques," Proc. 9th Australasian User Interface Conference (AUIC2008), School of Computer and Information Science, University of South Australia, pp. 19-28.
Taffinder, et al. "Validation of virtual reality to teach and assess psychomotor skills in laparascopic surgery: results from randomized controlled studies using the MIST VR laparascopic simulator," Medicine Meets Virtual Reality, pp. 124-133 (1998).
Theoktisto, et al. "Enhancing collaboration in virtual reality applications," Computers and Graphics, vol. 29(5), pp. 704-718 (2005).
Viciana-Abad, et al. "A preliminary study of presence in virtual reality training simulation for medical emergencies," Medicinal Meets Virtual Reality, vol. 12, pp. 394-396 (2004).
Vogt, et al. "An ar system with intuitive user interface for manipulation and visualization of 3d medical data," Stud Health Technol Inform., vol. 98, pp. 397-403 (2004).
Wann, et al. "Natural problems for stereoscopic depth perception in virtual environments," Vision Research, vol. 35(19), pp. 2731-2736 (1995).
Non-Final Office Action issued Jan. 7, 2013 for U.S. Appl. No. 13/208,926, filed Aug. 12, 2011 and published as U.S. 2013/0038632 on Feb. 14, 2013 (Inventor—Dillavou; Applicant—Vipaar, LLC) (pp. 1-13).
Response to Non-Final Office Action filed Apr. 29, 2013 for U.S. Appl. No. 13/208,926, filed Aug. 12, 2011 and published as U.S. 2013/0038632 on Feb. 14, 2013 (Inventor—Dillavou; Applicant—Vipaar, LLC) (pp. 1-11).
Final Office Action issued Jul. 22, 2013 for U.S. Appl. No. 13/208,926, filed Aug. 12, 2011 and published as U.S. 2013/0038632 on Feb. 14, 2013 (Inventor—Dillavou; Applicant—Vipaar, LLC) (pp. 1-14).
Response After Final Office Action filed Nov. 19, 2013 for U.S. Appl. No. 13/208,926, filed Aug. 12, 2011 and published as U.S. 2013/0038632 on Feb. 14, 2013 (Inventor—Dillavou; Applicant—Vipaar, LLC) (pp. 1-12).
Non-Final Office Action issued Jan. 2, 2014 for U.S. Appl. No. 13/208,926, filed Aug. 12, 2011 and published as U.S. 2013/0038632 on Feb. 14, 2013 (Inventor—Dillavou; Applicant—Vipaar, LLC) (pp. 1-16).
Amendment and Response to Non-Final Office Action filed Jul. 3, 2014 for U.S. Appl. No. 13/208,926, filed Aug. 12, 2011 and published as U.S. 2013/0038632 on Feb. 14, 2013 (Inventor—Dillavou; Applicant—Vipaar, LLC) (pp. 1-11).
Petition for Revival filed Jul. 3, 2014 for U.S. Appl. No. 13/208,926, filed Aug. 12, 2011 and published as U.S. 2013/0038632 on Feb. 14, 2013 (Inventor—Dillavou; Applicant—Vipaar, LLC) (pp. 1-2).
Non-Final Office Action issued Jun. 20, 2014 for U.S. Appl. No. 13/476,712, filed May 21, 2012 and published as U.S. 2013/0308827 on Nov. 21, 2013 (Inventor—Dillavou; Applicant—Vipaar, LLC) (pp. 1-13).
Non-Final Office Action issued Nov. 23, 2012 for U.S. Appl. No. 12/600,805, filed Aug. 11, 2010 and published as U.S. Pat. No. 8,520,024 on Aug. 27, 2013 (Inventor—Dillavou; Applicant—Vipaar, LLC) (pp. 1-13).
Amendment and Response to Non-Final Office Action filed Mar. 25, 2013 for U.S. Appl. No. 12/600,805, filed Aug. 11, 2010 and published as U.S. Pat. No. 8,520,024 on Aug. 27, 2013 (Inventor—Dillavou; Applicant—Vipaar, LLC) (pp. 1-15).
Notice of Allowance issued May 16, 2013 for U.S. Appl. No. 12/600,805, filed Aug. 11, 2010 and published as U.S. Pat. No. 8,520,024 on Aug. 27, 2013 (Inventor—Dillavou; Applicant—Vipaar, LLC) (pp. 1-9).
Issue Notification issued Aug. 7, 2013 for U.S. Appl. No. 12/600,805, filed Aug. 11, 2010 and published as U.S. Pat. No. 8,520,024 on Aug. 27, 2013 (Inventor—Dillavou; Applicant—Vipaar, LLC) (pp. 1-1).
9European Search Report issued Sep. 15, 2011 for European Patent Application No. 2008826034, which was filed on May 19, 2008 (Inventor—Guthrie; Applicant—The UAB Research Foundation) (pp. 1-9).
International Preliminary Report on Patentability issued Nov. 24, 2009 for International Patent Application No. PCT/US2008/064118, which was filed on May 19, 2008 and published as WO 2009/005901 on Jan. 8, 2009 (Inventor—Guthrie; Applicant—The UAB Research Foundation) (pp. 1-6).
International Search Report and Written Opinion issued Dec. 17, 2008 for International Patent Application No. PCT/US2008/064118, which was filed on May 19, 2008 and published as WO 2009/005901 on Jan. 8, 2009 (Inventor—Guthrie; Applicant—The UAB Research Foundation) (pp. 1-8).
International Search Report and Written Opinion issued Oct. 16, 2012 for International Patent Application No. PCT/US2012/050238, which was filed on Aug. 10, 2012 and published as WO 2013/025457 on Feb. 21, 2013 (Inventor—Dillavou; Applicant—Vipaar, LLC) (pp. 1-2).
International Preliminary Report on Patentability issued Feb. 18, 2014 for International Patent Application No. PCT/US2012/050238, which was filed on Aug. 10, 2012 and published as WO 2013/025457 on Feb. 21, 2013 (Inventor—Dillavou; Applicant—Vipaar, LLC) (pp. 1-6).
International Search Report issued Dec. 2, 2013 for International Patent Application No. PCT/US2013/041967, which was filed on May 21, 2013 and published as WO 2013/177125 on Nov. 28, 2013 (Inventor—Dillavou; Applicant—Vipaar, LLC) (pp. 1-3).

(56) References Cited

OTHER PUBLICATIONS

Newman et al. A Desk Supporting Computer-based Interaction with Paper Documents; Rank Xerox EuroPARC, United Kingdom, 1992 ACM 0-89791-513-5/92/0005-0587, pp. 587-592.
Greenberg, An Annotated Bibliography of Computer Supported Cooperative Work, SIGCHI Bulletin, Jul. 1991, vol. 23, No. 3, pp. 29-62.
Ishii et al. ClearBoard: A Seamless Medium for Shared Drawing and Conversation with Eye Contact, NTT Human Interface Laboraties, Kanagawa, Japan, 1992 ACM 0-89791-513-5/92/0005-0525, pp. 525-532, Exh. 705-706.
Takemura et al. Cooperative Work Environment Using Virtual Workspace, ATR Communication Systems Research Laboratories, Kyoto, Japan, 1992 ACM 0-89791-543-7/92/0226; CSCW 92 Proceedings, Nov. 1992, pp. 226-232.
Greenberg, CSCW '92 Formal Video Program, Department of Computer Science, University of Calgary, 1992, pp. 9-10.
Chang, et al., Design and Model for a Computer Supported Cooperative Environment for CASE and CAD Applications, Department of Computer Science and Engineering, Auburn University, 1997 ACM 0-8971-925-4, pp. 191-198.
Kobayashi et al., DispLayers: Multi-Layer display Technique to Enhance Selective Looking of Overlaid Images, NTT Human Interface Laboratories, Kanagawa, Japan, p. 66.
Steitz et al., DOLPHIN: Integrated Meeting Support Across Local and Remote Desktop Environments and LiveBoards, IPSI—Integrated Publication and Information Systems Institute, GMD—German National Research Center for Computer Science, Conference Paper Oct. 1994, 1994 ACM 0-89791-689-1/94; pp. 345-358.
Ishii, et al., Beyond Videophones: Team WorkStation-2 for Narrowband ISDN, NTT Human Interface Laboratories, Japan; Proceedings of the Third European Conference on Computer supported Cooperative Work Sep. 13-17, 1993, Milan, Italy, ESCSW '93, pp. 325-326.
Ishii, et al., Integration of Inter-personal Space and Shared Workspace: ClearBoard Design and Experiments, NTT Human Interface Laboraties and University of California, Irvine, ACM Transactions on Information Systems, vol. 11, No. 4, Oct. 1993, pp. 349-375.
Yamazaki, et al., GestureLaser and GestureLaser Car, Devleopment of an Embodied Space to Support Remote Instruction, Proceedings of the Sixth European Conference on Computer-Supported Cooperative Work, Sep. 12-16, 1999, Copehangen Denmark; 1999 Kluwer Academic Publishers, pp. 239-258.
Hayne, et al., Implementing Gesturing With Cursors in Group Support Systems, Journal of Management Information Systems, Winter 1993-94, vol. 10, No. 3, pp. 43-61.
Ishii et al., Iterative Design of Seamless Collaboration Media, Communications of the ACM, Aug. 1994, vol. 17, No. 8, pp. 83-97.
Ishii et al., Towawrd an Open Shared Workspace: Computer and Video Fusion Approach of Teamworkstation, Communications of the ACM, Dec. 1991, vol. 34, No. 12, pp. 37-50.
Ishii, Integration of Shared Workspace and Interpersonal Space for Remote Collaboration, Computer Supported Cooperative Work, 1999 John Wiley & Sons, Ltd. pp. 83-101.
Ishii, Translucent Multiuser Interface for Realtime Collaboration, IEICE trans. Fundamentals, vol. E75-A, No. 2—Feb. 1992, pp. 122-131.
DeVincezi, et al., Kinected Conference: Augmenting Video Imaging with Calibrated Depth and Audio, CSCW 2011, Mar. 19-23, 2011, Hangzhou, China, ACM 978-1-4503-0556-3/11/03, pp. 621-624.
Foreman, Managing Data in Distributed Multimedia Conferencing Applications, IEEE MultiMedia, Oct.-Dec. 2002, pp. 30-37.
Kuzuoka, Spatial Workspace Collaboration: A Sharedview Video Support System for Remote Collaboration Capability, Department of Mechano-Informatics, University of Tokyo, 1992 ACM 0-89791-513-5/92/005-0533, pp. 533-540.
Graves, et al. Supporting Learners in a Remote CSCL Environment: the Importance of Task and Communication, Dept. of Computer Science, University of British Columbia, 11 pgs.

Ishii, Position Paper for ECSCW '91 Workshop on Open CSCW Systems Toward an Open Shared Workspace: Computer and Video Fusion Approach of Team WorkStation, NTT Human Interface Laboratories, Kanagawa, Japan, 4 pgs.
Apperley, et al. Use of Video Shadow for Small Group Interaction Awareness on a Large Interactive Display Surface, The Computer Science Department, University of Waikato, New Zealand, 2002, Australian Computer Society, Inc., 10 pgs.
Kling, Cooperation, Coordination and Control in Computer-Supported Work, Communications of the ACM, Dec. 1991, vol. 34, No. 12, pp. 83-88.
Rosenberg, Update on National Science Foundation Funding of the "Collaboratory", Communications of the ACM, Dec. 1991, vol. 34, No. 12, p. 83.
Norman, Collaborative Computing: Collaboration First, Computing Second, Communications of the ACM, Dec. 1991, vol. 34, No. 12, p. 88-90.
Pendergast, A Comparative Analysis of Groupware Application Protocols, ACM SIGCOMM, Computer Communication Review, pp. 28-40.
Press, Collective Dynabases, Communications of the ACM, Jun. 1992, vol. 35, No. 6, pp. 26-32.
Reeves et al., Supporting Communication Between Designers with Artifact-Centered Evolving Information Spaces, Department of Computer Science and Institute of Cognitive Science, University of Color-401ado, 1992 ACM 0-89791-543-7/9210010/0394, CSCW 92 Proceedings, Nov. 1992, pp. 394.
Tani et al., Courtyard: Integrating Shared Overview on a Large Screen and Per-User Detail on Individual Screens, Hitachi Research Laboratory, Hitachi, Ltd., Human Factors in Computing Systems, 1994 ACM 0-89791-650-6/94/0044, pp. 44-50.
Takemura et al., Cooperative Work Environment Using Virtual Workspace, ATR Communication Systems Research Laboratories, 1992 ACM 0-089791-543-7/92/001010226, CSCW 92 Proceedings, Nov. 1992, pp. 226-232.
Wellner, Interacting With Paper on the Digital Desk, Communication of the ACM, Jul. 1993, vol. 36, No. 7, pp. 87-96.
Wiberg, RoamWare: An Integrated Architecture for Seamless Interaction in Between Mobile Meetings, Department of Informatics, Umea University, Sweden, 2001 acm 1-58113-294-8/01/0009, pp. 288-297.
Veltman, Frontiers in Electronic Media, Interactions Jul. & Aug. 1997, pp. 32-66.
Fouss, et al., Classifying Groupware, Department of Computer Science and Software Engineering, Auburn University, 2000 ACM 1-58113-250-6/00/0004, pp. 117-124.
Mandviwalla et al., What Do Groups Need? A Proposed Set of Generic Groupware Requirements, 1994 ACM 1073-0516194/ 0900-0245, ACM Transactions on Computer-Human Interaction, vol. 1, No. 3, Sep. 1994, pp. 245-268.
Bly, et al., Media Spaces: Bringing People Together in a Video, Audio, and Computing Environment, Communications of the ACM, Jan. 1993, vol. 36, No. 1, pp. 27-47.
Ishii, et al., Integration of Inter-personal Space and Shared Workspace: ClearBoard Design and Experiments, NTT Human Interface Laboraties and University of California, Irvine, CSCW 92 Proceedings, Nov. 1992, pp. 33-42.
Anupam, et al., Collaborative Multimedia Scientific Design in SHASTRA, Department of Computer Sciences, Purdue University, West Lafayette, Indiana, 12 pgs.
Allen, Groupware and social Reality, Department of Information and Computer Science, University of California, Irvine, computers & Society, vol. 22, No. 1-4, Oct. 1992, pp. 24-28.
Hunter, et al., WaaZam! Supporting Creative Play at a Distance in Custo-1206mized Video Environments, CHI 2014, Apr. 26-May 1, 2014, Toronto, ACM 978-1-4503-2473-1/14/04, pp. 1197-1206.
Franck, et al., Putting Innovation to Work: Adoption Strategies for MultiMedia Communication Systems, communication of the ACM, Dec. 1991, vol. 34, No. 12, pp. 53-63.

(56) References Cited

OTHER PUBLICATIONS

Gross, Recognizing and Interpreting Diagrams in Design, Division of Environmental Design and Institute of Cognitive Science, University of Colorado, 1994 ACM 0-89791-733-2/94/0010, pp. 88-94.

* cited by examiner

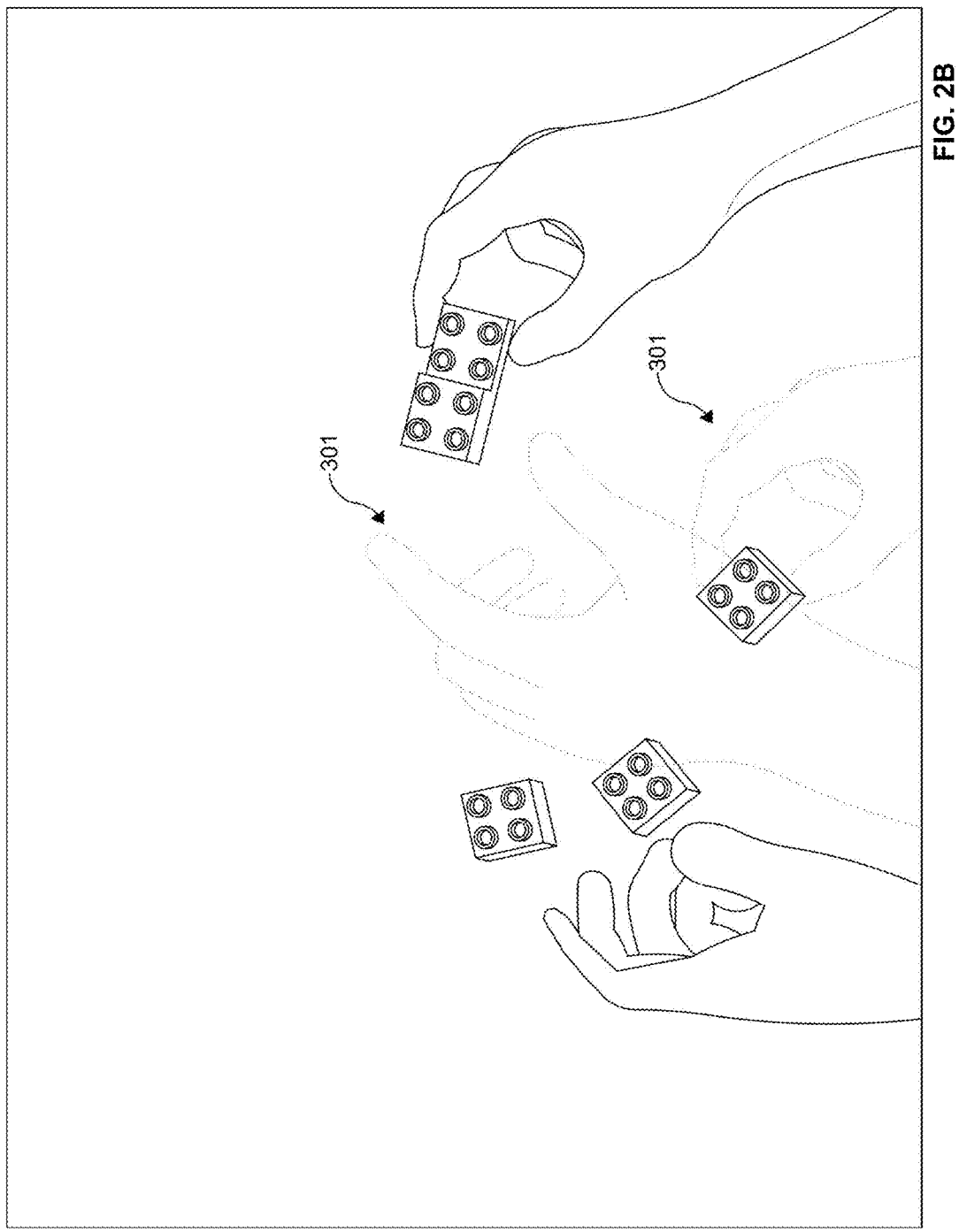

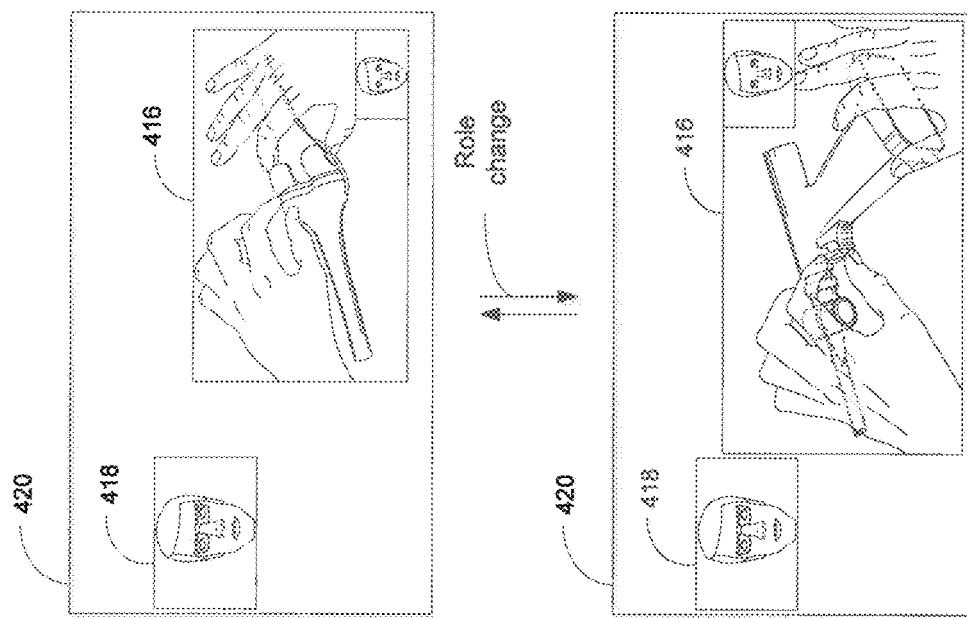
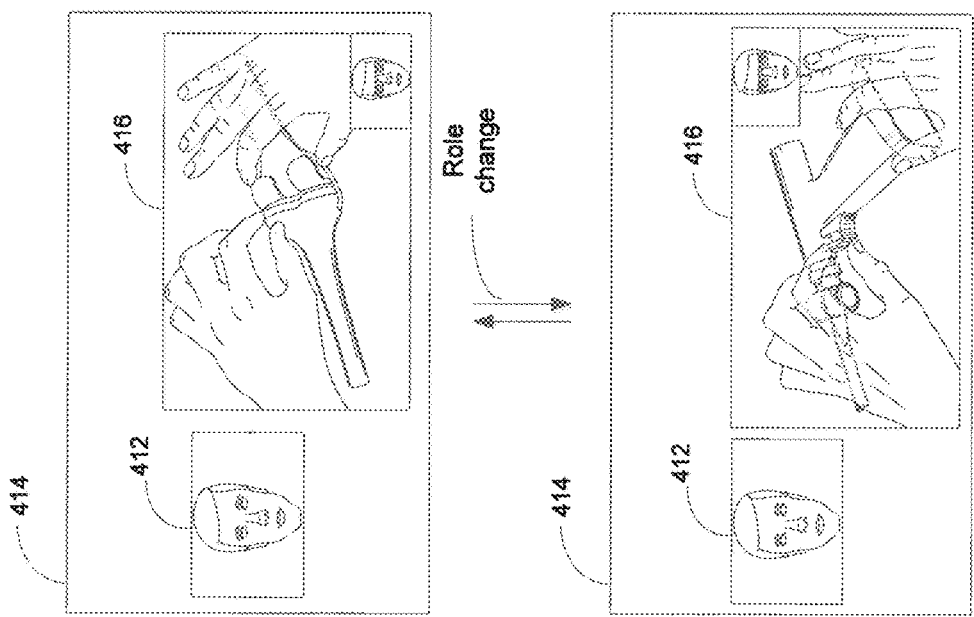
FIG. 4B

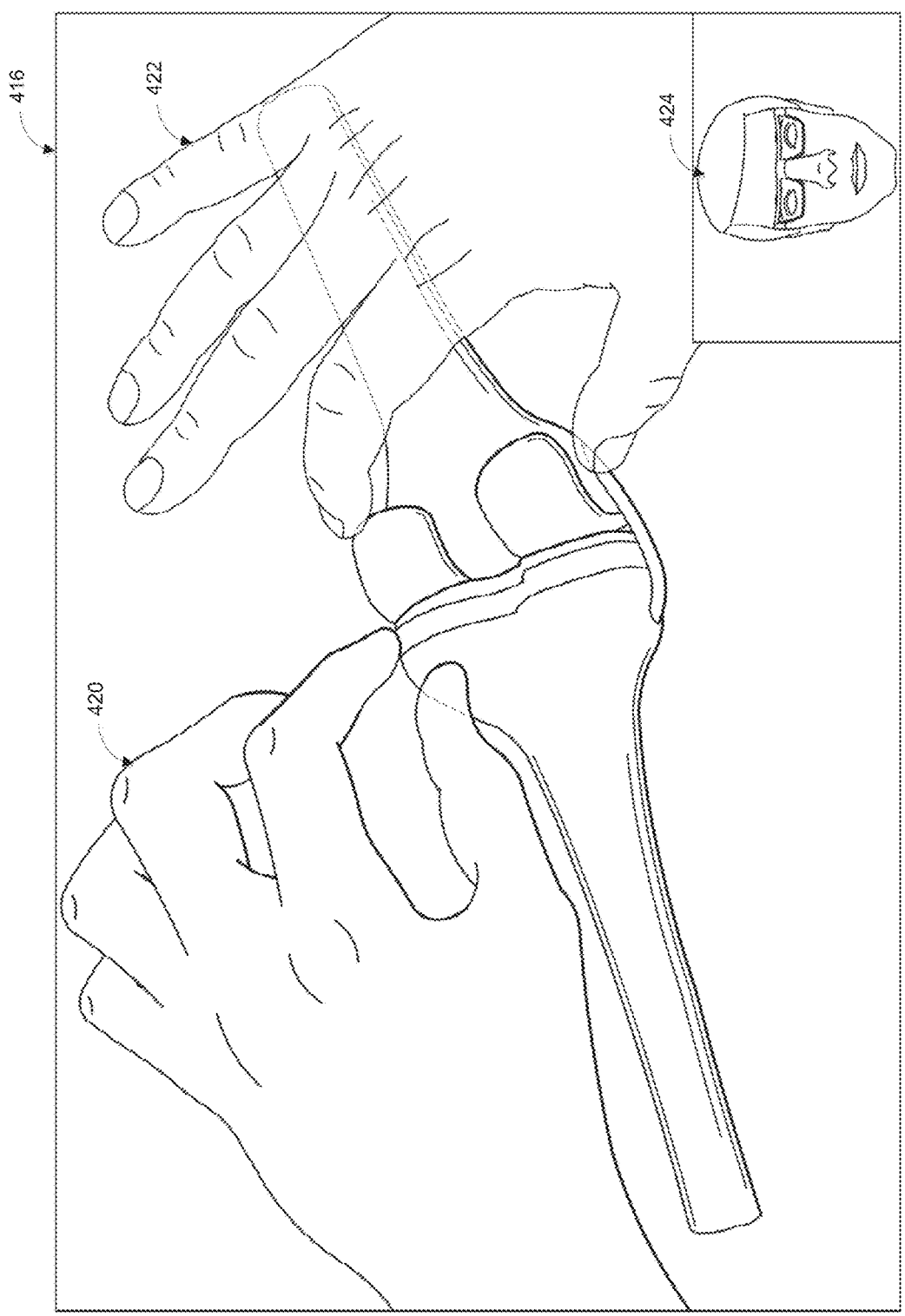

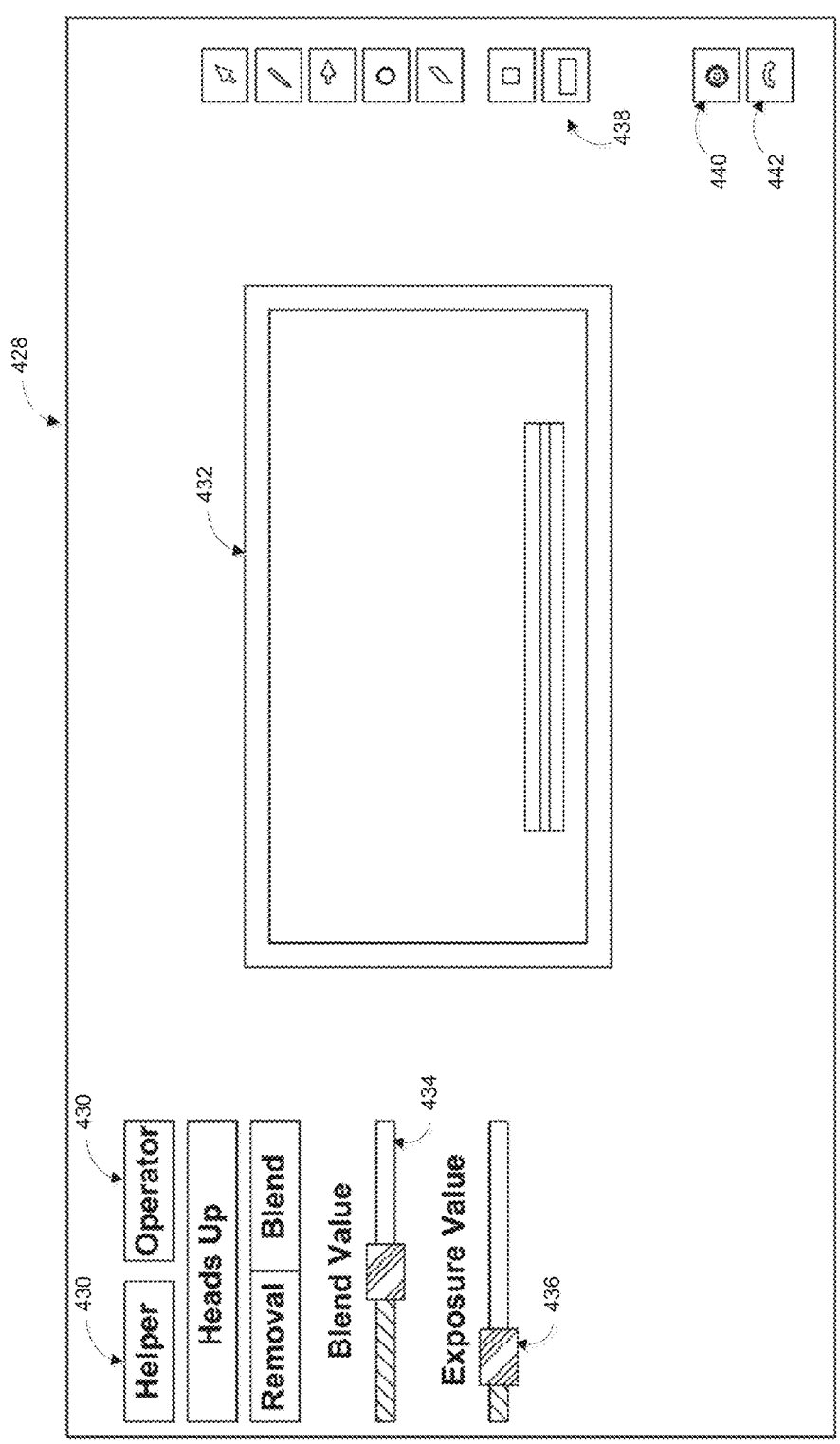

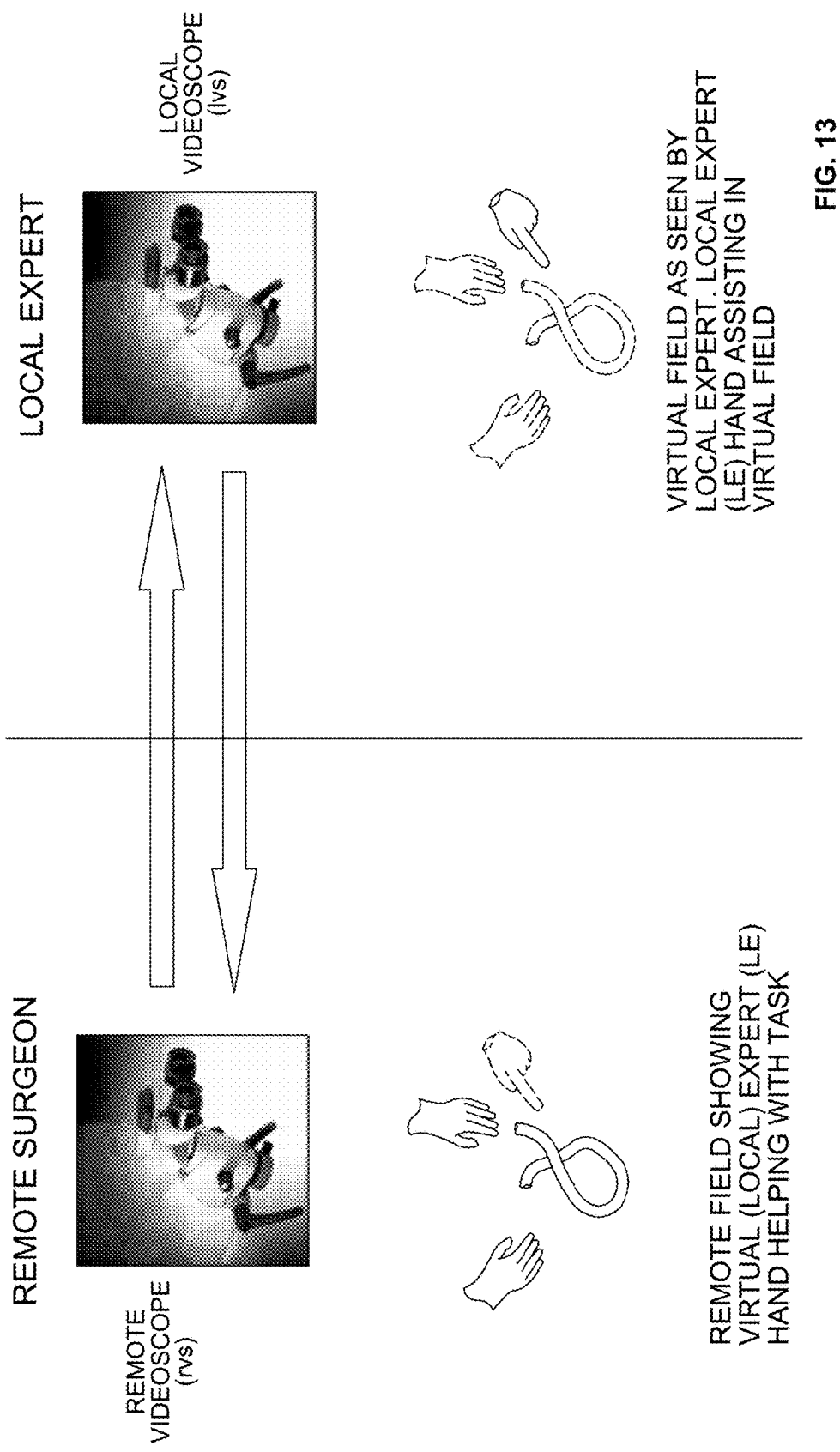

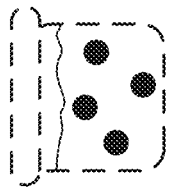

Slices of MRI scan of beaker of object.

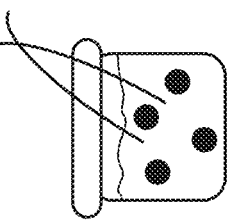

Computer volume rendering of "virtual beaker."

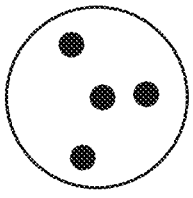

Objects suspended in beaker of opaque gelatin. Objects are not visible to the eye.

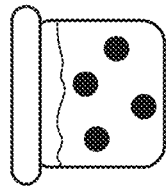

User interface within the videoscope enables user to scale/rotate virtual beaker so that it is superimposed onto real beaker.

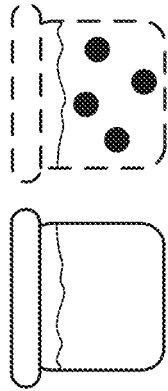

Once merged, the user can use the virtual beaker to navigate within the real beaker.

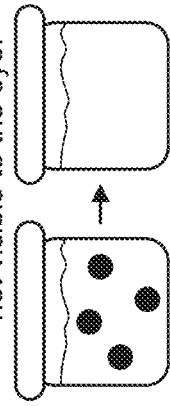

Real and virtual beaker as viewed through a videoscope.

FIG. 14

SYSTEM AND METHOD FOR ROLE-SWITCHING IN MULTI-REALITY ENVIRONMENTS

BACKGROUND

Mixed reality systems can enable physically separated users to engage in multi-reality sessions in real-time. These systems may perform some degree of image processing to enable such sessions. Users participating in multi-reality sessions with other concurrent users may be operating in a particular role relative to the other users. However, mixed reality systems do not provide a sufficient means to designate various roles for one or more users. Accordingly, there is a need for a means to enable a user to designate a role in real-time.

SUMMARY

It is to be understood that both the following general description and the following detailed description are exemplary and explanatory only and are not restrictive, as claimed. Disclosed are systems and methods for role switching in multi-reality environments. In an aspect, the systems and methods of the present invention can comprise designating a role for one or more users. As such, processing of one or more images or video can be configured for the designated role.

Methods are described for role designation. One method comprises: rendering a common field of interest that reflects a presence of a plurality of elements, wherein at least one of the elements is a remote element located remotely from another of the elements; receiving a role designation; and updating the common field of interest based upon the role designation.

Another method comprises: generating a first image representing a first element; generating a second image representing a second element disposed remotely from the first element; receiving a role designation; and rendering a composite image including the first image and the second image, wherein a display characteristic of at least one of the first image and the second image relative to the other of the first image and the second image is modified based upon the role designation.

A system for image processing is described. The system comprises: a display configured for displaying a common field of interest; a sensor configured for obtaining image data; a processor in signal communication with the display and the sensor, wherein the processor is configured to perform steps comprising, rendering a common field of interest that reflects a presence of a plurality of elements, wherein at least one of the elements is a remote element located remotely from another of the elements; receiving a role designation; and updating the common field of interest based upon the role designation; and outputting the common field of interest to the display.

Additional advantages will be set forth in part in the description which follows or may be learned by practice. The advantages will be realized and attained by means of the elements and combinations particularly pointed out in the appended inventive concepts. It is to be understood that both the foregoing general description and the following detailed description are exemplary and explanatory only and are not to be considered restrictive.

BRIEF DESCRIPTION OF THE DRAWINGS

The accompanying drawings, which are incorporated in and constitute a part of this specification, illustrate embodiments and together with the description, serve to explain the principles of the methods and systems provided:

FIG. 2B illustrates a local expert assisting a remote user;
FIG. 4B illustrates an exemplary virtual interactive presence schematic;
FIG. 4C illustrates an exemplary user interface;
FIG. 4E illustrates an exemplary user interface;
FIG. 13 illustrates virtual presence in a remote surgical environment;
FIG. 14 illustrates merging of medical imaging with an operative field.

DETAILED DESCRIPTION

Figure 1:
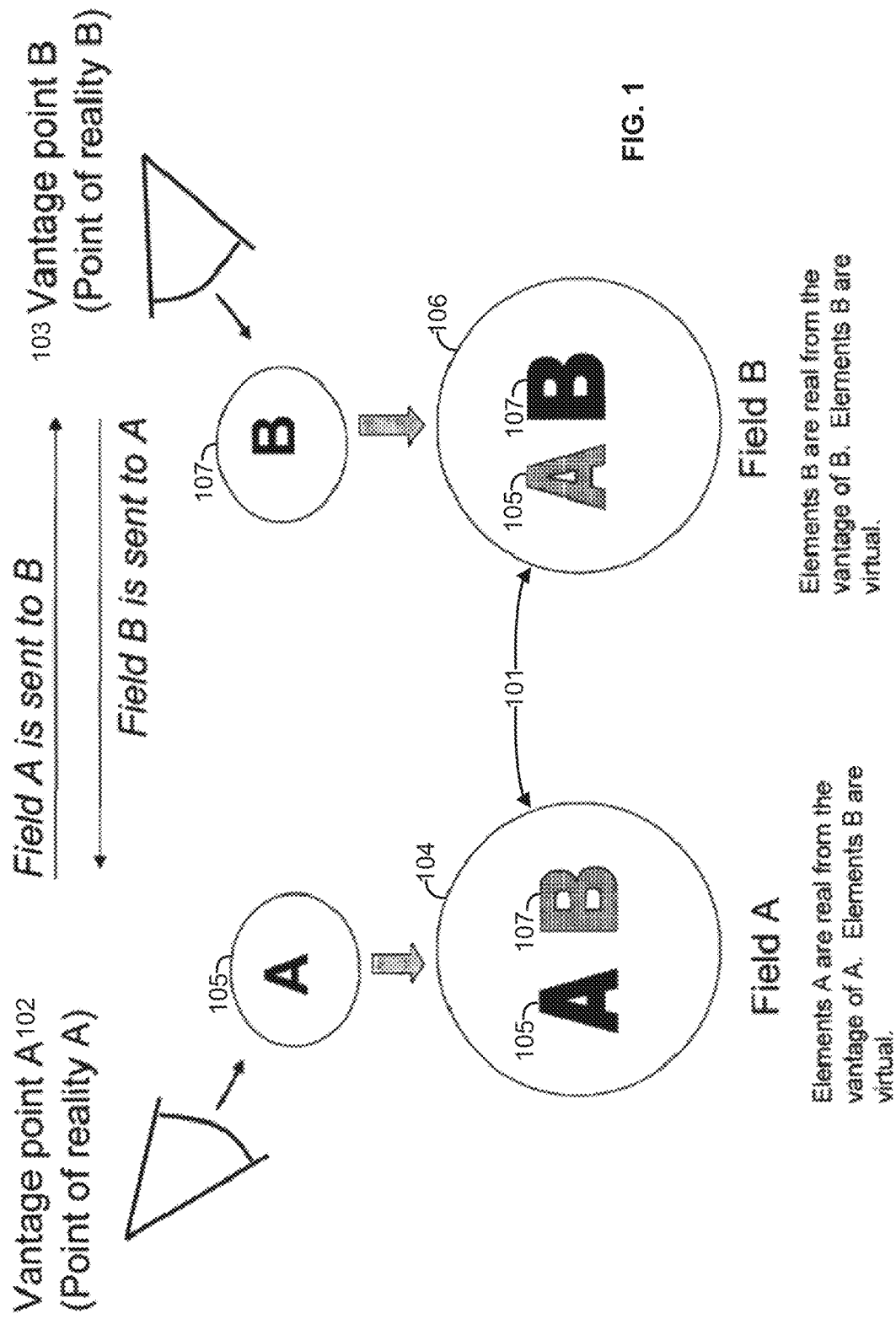
FIG. 1 illustrates virtual interactive presence.

Before the present methods and systems are disclosed and described, it is to be understood that the methods and systems are not limited to specific synthetic methods, specific components, or to particular compositions, as such may, of course, vary. It is also to be understood that the terminology used herein is for the purpose of describing particular embodiments only and is not intended to be limiting.

As used in the specification and the appended inventive concepts, the singular forms "a," "an" and "the" include plural referents unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

Disclosed are methods and systems for role designation with multiple video streams. The disclosed methods and systems can utilize virtual reality. Virtual reality (VR) refers to a computer-based application which provides a human-computer interface such that the computer and its devices create a sensory environment which is dynamically controlled by the actions of the individual, so that the environment appears "real" to the user. With VR, there is communication between a computer system and a user. The computer creates a sensory environment for the user to experience which may be, in one aspect, multisensory (although this is not essential) and the computer creates a sense of reality in response to user inputs.

In one exemplary aspect, the system disclosed can utilize at least two types of VR, Immersive and Non-immersive. Immersive VR creates the illusion that the user is actually in a different environment. In one aspect, the system accomplishes this through the use of such devices as Head Mounted Displays (HMD's), earphones, and input devices such as gloves or wands. In another aspect, in order to enhance to realism of the experience, a plurality of Degrees of Freedom (DOF's) are utilized, which the software can simulate. Generally, the more the DOF's, the better the realism of the experience. Exemplary DOF's include, without limitation: X,Y,Z, roll, pitch, and yaw.

Non-immersive VR creates an environment that is differentiable from the user's surrounding environment. It does not give the illusion that the user is transported to another world. Non-immersive VR works by creating a 3-dimensional image and surround sound through the use of stereo projection systems, computer monitors, and/or stereo speakers. Non-immersive VR can be run from a personal computer without added hardware.

In one aspect, movement in Immersive VR can be realized by a system through the use of optical, acoustical, magnetic, or mechanical hardware called trackers. Preferably, the input devices have as many of these trackers as possible, so that movement can be more accurately represented. For instance, virtual gloves can have up to 3 trackers for each index, and more for the palm and wrist, so that the user can grab and press objects. In one aspect, the trackers can be equipped with positioning sensors, that tell a computer which direction the input is facing and how the input device is tilted in all directions. This gives a sensor with six degrees of freedom.

Output devices bring the user to the virtual world. An example of an output device that can be used in the present system include, without limitation, head mounted displays (HMD) in the form of glasses or goggles, which allow a user to wear a display system on their head. One approach to the HMD is to use a single Liquid Crystal Display (LCD), wide enough to cover both eyes. Another approach is to have two separated displays—one for each eye. This takes somewhat more computer power, since the images displayed are different. Each display has a separate image rendered from the correct angle in the environment. Eye-tracking can be combined with HMDs. This can allow, for example, surgeons to move their eyes to the part of an image they want to enhance.

Another example of an output device that can be used in an embodiment of the present system is shuttered glasses. This device updates an image to each eye every other frame, with the shutter closed on the other eye. Shuttered glasses require a very high frame rate in order to keep the images from flickering. This device is used for stereo monitors, and gives an accurate 3-d representation of a 2-d object, but does not immerse the user in the virtual world.

Another output device that can be used in an embodiment of the present system is a screen with multiple projectors. The screen can be either a plane or bent. A challenge when using multiple projectors on the same screen is that there can be visible edges between the projections. This can be remedied be using a soft-edge system wherein the projection goes more and more transparent at the edges and the projections overlap. This produces an almost perfect transition between the images. In order to achieve a desired 3D effect, shuttered glasses can be used. Special glasses can be used, that alternate between making the glass either completely opaque or completely transparent. When the left eye is opaque, the right, one is transparent. This is synchronized to the projectors that are projecting corresponding images on the screen.

In another aspect, a Cave Automatic Virtual Environment (CAVE) can also be used in the present system. A CAVE can use mirrors in a cube-shaped room to project stereo images onto the walls, giving the illusion that you are standing in a virtual world. The world is constantly updated using trackers, and the user is allowed to move around almost completely uninhibited.

Disclosed are methods and systems for role designation. Such methods and systems can render a number of elements/participants virtually present into a field of interest in a manner such that the users can interact for any given purpose, such as the delivery of remote expertise. A field of interest can comprise varying amounts of "real" and "virtual" elements, depending on a point of view. Elements can include any "real" or "virtual" object, subject, participant, or image representation. Various components of the disclosed methods and systems are illustrated in FIG. 1.

A common field of interest 101 can be a field within which elements are physically and/or virtually present. Point of Reality (or Point of View) can refer to the vantage of the element/participant that is experiencing the common field of interest. In FIG. 1, exemplary points of reality, or points of view, are shown at 102 and 103, representing displays. The common field of interest 101 can appear similar from both vantages, or points of view, but each comprises differing combinations of local (physical) and remote (virtual) elements/participants.

Local elements can be elements and/or participants which are physically present in the common field of interest. In FIG. 1, element A 105 is a local element for field A 104 and is physically present in field A 104. Element B 107 is a local element for field B 106 and is physically present in field B 106. It is understood that virtual elements (not shown) can be inserted or overlaid in field A 104 and/or field B 106, as desired.

Remote elements can be elements and/or participants that are not physically present in the common field of interest. They are experienced as "virtually present" from any other local vantage point. As shown in FIG. 1, element B 107 is a remote element to field A 104 and is virtually present in field A 104. Element A 105 is a remote element in field B 106 and is virtually present in field B 106.

Figure 2A:
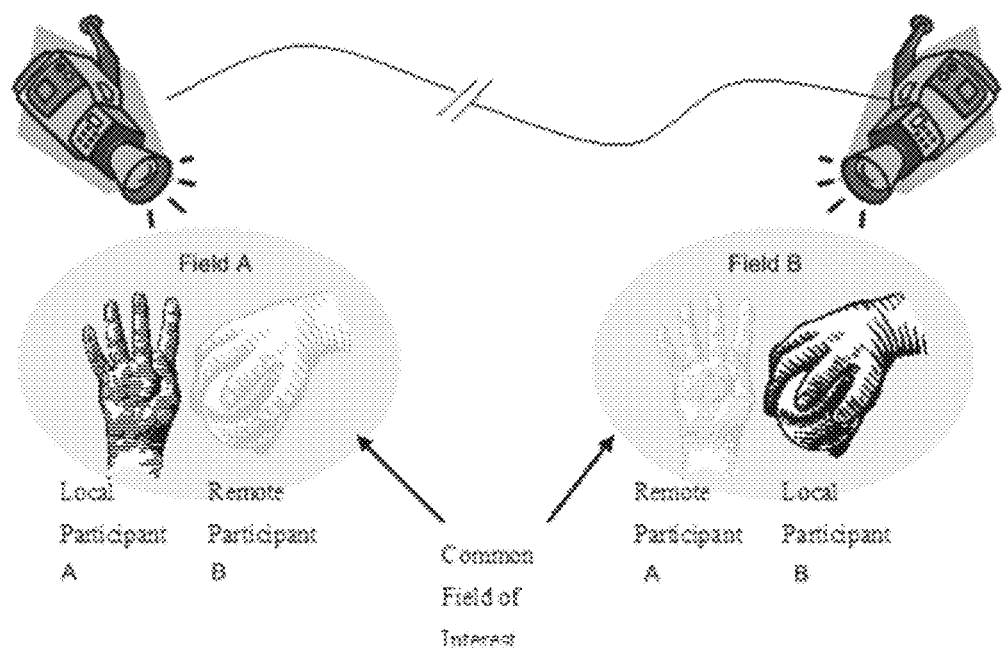
FIG. 2A illustrates virtual interactive presence.

Methods for rendering a virtual interactive presence by combining local and remote elements and/or participants can comprise one or more of the following steps. A common local field can be rendered in a manner that reflects the presence of the field, elements and/or participants. As shown in FIG. 2A, Participant A can experience real elements in field A through a viewer. The common local field can be rendered such that it is experienced remotely in a manner that enables remote participants to experience it similarly to the local persons. As shown in FIG. 2A, this is illustrated by Participant A experiencing element B as virtually present in field A.

Remote persons can insert themselves and/or interact with the virtual field as rendered to them. For example, Participant A can insert hands, instruments, etc. into field A and interact with the virtual element(s) B. Viewer B can view a 'virtual compliment' to this, with Viewer B's real elements interacting with Participant A's virtual elements.

The common local field can be continuously updated such that the presence of the remote participants can be rendered in real time. For example, the remote scene can be the most up-to-date available with the time lag between the remote capture and the local render kept as low as possible. Conversely, if there is a need to introduce a timing difference, this can be accomplished as well.

The common local field can be scaled to a size and depth to meaningfully match the local scene. And the common local field can be configurable, such that remote elements can be made more or less transparent, removed entirely, or otherwise altered to suit the needs of the local user.

Each field is captured by a digital camera. The resulting image is physically distorted from its reality, based upon the physical characteristics of the camera. A processor, therefore, receives and displays a "physically" distorted version of the local reality. Likewise, a digital camera also captures the remote field(s), but the incoming stream is relayed through a transmission device and across a network. The processor, therefore, receives the remote stream that contains both physical and transmission-based distortion. The processor must then apply a series of transformations that removes the physical and transmission-based distortion from the common local field.

The local participants can experience the virtually present participants in a manner that enables continuous interaction in the common local field. FIG. 2B illustrates a local expert assisting a remote user. The hands of the local expert 201 are slightly transparent and superimposed into the field that is viewed by the remote user. The remote user can view the local expert's hands, the remote user's hands and a puzzle located at the remote user's location. The local expert is assisting the remote user in assembling a puzzle.

Figure 3:
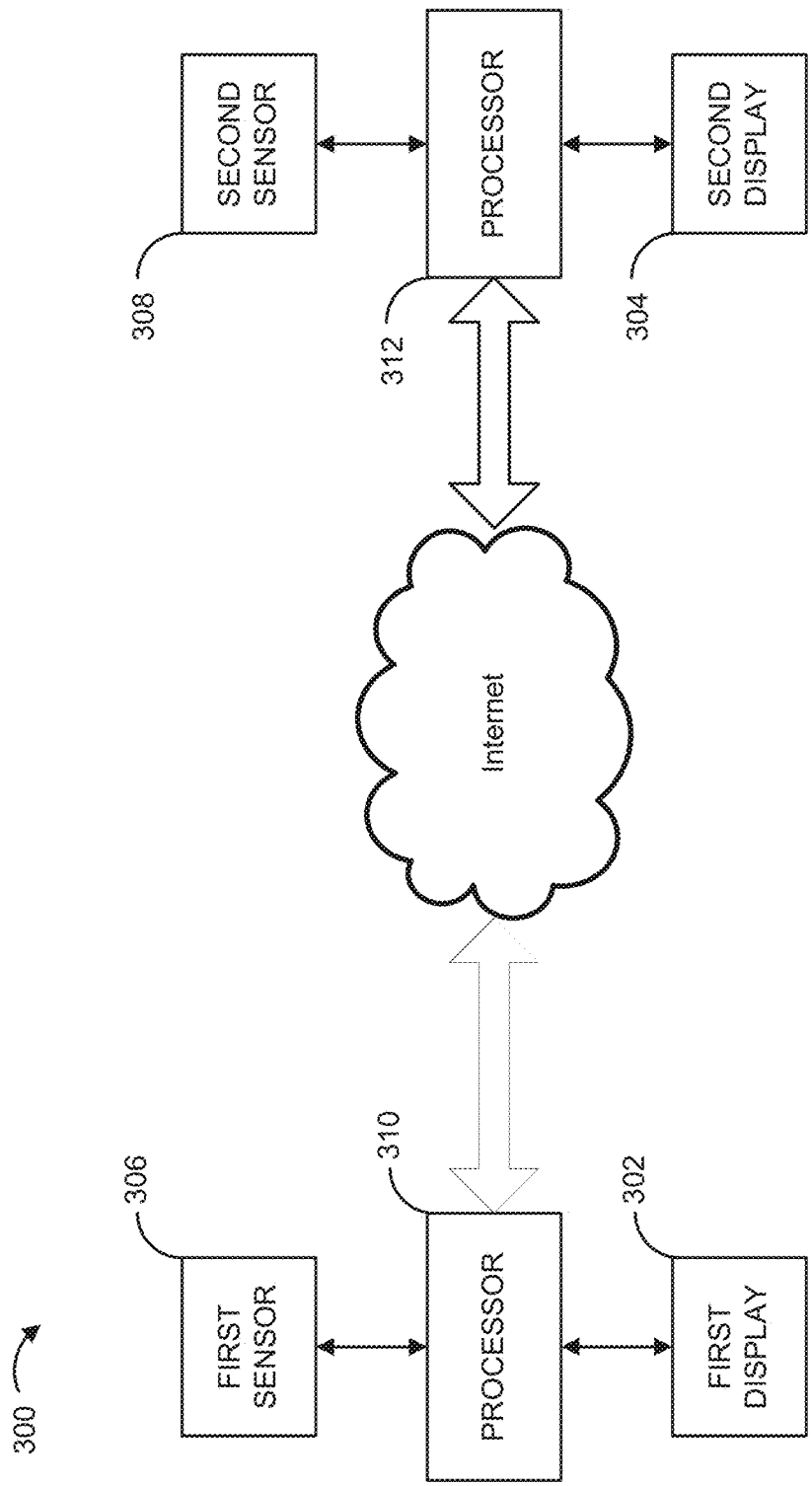
FIG. 3 illustrates an exemplary system architecture.

FIG. 3 illustrates an exemplary image processing system 300. As shown, the system 300 can comprise a first display 302 and a second display 304 configured for displaying one or more of an image, a video, a composite video/image, and a common field of interest, for example. However, it is understood that any number of displays can be included in the system 300. In certain aspects, the second display 304 can be disposed remotely from the first display 302. As an example, each of the first display 302 and the second display 304 can be configured to render the common field of interest thereon. As a further example, each of the first display 302 and the second display 304 can be configured to render at least one of the local field and the remote field thereon. In certain aspects, at least one of the first display 302 and the second display 304 can be a VIP display, as described in further detail herein. However, it is understood that each of the first display 302 and the second display 304 can be any type of display including a monoscopic display and a stereoscopic display, for example. It is understood that any number of any type of display can be used.

A first sensor 306 can be in signal communication with at least the first display 302 and can be configured for obtaining image data such as a virtual presence data, for example. In certain aspects, the first sensor 306 can be one or more of a camera, an infrared sensor, a light sensor, a RADAR device, a SONAR device, a depth scan sensor, and the like. It is understood that the first sensor 306 can be any device or system capable of capturing/obtaining an image data representative of at least one of a "real" element and a "virtual" element.

A second sensor 308 can be in signal communication with at least the second display 304 and can be configured for obtaining image data such as virtual presence data, for example. In certain aspects, the second sensor 308 can be one or more of a camera, an infrared sensor, a light sensor, a RADAR device, a SONAR device, a computed tomography device, a magnetic resonance imaging device, a depth scan sensor, and the like. It is understood that the second sensor 308 can be any device or system capable of capturing/obtaining an image data representative of at least one of a "real" element and a "virtual" element. It is further understood that any number of sensors can be used.

A plurality of processors 310, 312 can be in direct or indirect signal communication with at least one of the first display 302, the second display 304, the first sensor 306, and the second sensor 308. Each of the processors 310, 312 can be configured to render the image data collected by the sensors 306, 308 onto at least one of the displays 302, 304. It is understood that the processors 310, 312 can be configured to modify the image data and the resultant image for transmission and display. It is further understood that any number of processors can be used, including one. In certain aspects, the system 300 comprises only the processor 310, 312 in data communication with each other.

In certain aspects, each of the displays 302, 304 can comprise an associated one of the processors 310, 312 for rendering images onto the displays 302, 304. Each of the processors 310, 312, or another system comprising a processor, can communicate with each other through a network connection. For example, remote sites can connect via the Internet or other network. Tasks can be divided amongst each of the processors 310, 312. For example, one of the processors 310, 312 can be configured as a graphics processor or graphics server and can gather images from one of the sensors 306, 308 and/or a network server, perform an image composition tasks, and drive one or more of the displays 302, 304.

In an aspect, one or more of the processors 310, 312 can be configured to render an image. As an example, one or more of the processors 310, 312 can be configured to render a common field of interest that reflects a presence of a plurality of elements based upon the image data obtained by at least one of the sensors 306, 308. As a further example, at least one of the elements rendered in the common field of interest can be a remote element physically located remotely from another of the elements. The processors 310, 312 can also be configured to render/output the common field of interest to at least one of the displays 302, 304. As an example, the processors 310, 312 can render interaction between a remote user and a local user in the common field of interest. As a further example the presence of the remote element can be rendered in real time to the local user and the presence of a local element can be rendered in real time to the remote user.

In an aspect, one or more roles can be designated (e.g., defined, selected, received, generated) for one or more users. As an example a role can be designated as an abstraction that triggers a logical execution of one or more related programs by a processor. Such programs can, as an example, trigger a modification in the arrangement, organization, and/or presentation of a graphical user interface as displayed to a user. As another example, such programs can affect the processing of images and/or video by modifying the processing and/or post-processing of one or more images. As a further example, these programs can affect the rendering of images or video presented to one or more users.

In an aspect, processing of images can be implemented via a local processor prior to transmission to a remote processor. For example image compositing can occur at a local processor prior to transmission. As such, images and/or video received by a remote processor does not require compositing and can be accepted by a codec. As a further example, role designation can be implemented as an implicit role designation that occurs when a user of a system is compositing images versus a user that is merely receiving processed images.

In an aspect, a "helper" role can comprise the manipulation of data flow and data presentation. As an example, the helper role can comprise a particular arrangement of a software pipeline, such as a series of processing elements for which the output of one processing element is the input for the successive processing element. As a further example, images captured by a local camera and processed by a local processor can be merged with images captured by one or more remote cameras and processed by one or more remote processors in a manner that is associated with the helper role.

In an aspect, a particular texture processing can be associated with the helper role. As an example, an image can be mapped to a screen according to a specified coordinate transformation, wherein inputs are given as parameters to a fragment or pixel shatter. As a further example, one or more programmable functions associated with the helper role can be used to modify the traits (e.g., color, z-depth, alpha value) of one or more pixels of a given image. As another example, an image can have background subtraction, background removal, object detection, or similar algorithms applied to it for selective display of a region of the image.

In an aspect, for the helper role, one or more images captured by a local camera and processed by a local processor are rendered with an opacity of less than one, giving them a degree of transparency. One or more images captured by a remote camera and processed by a remote processor can be rendered with an opacity of about 1, thereby providing substantially complete opacity. As an example, one or more images of a remote "scene of interest" (e.g., surgery, maintenance site) can be rendered to fit a full display screen. As another example, one or more images of a remote user can be tiled or arranged on the display screen (i.e., picture-in-picture). As a further example, one or more images of a remote user's environment can be tiled or arranged on the display screen.

In an aspect, an "operator" role can comprise the manipulation of data flow and data presentation. As an example, the operator role can comprise a particular arrangement of a software pipeline, such as a series of processing elements for which the output of one processing element is the input for the successive processing element. As a further example, images captured by a local camera and processed by a local processor can be merged with images captured by one or more remote cameras and processed by one or more remote processors in a manner that is associated with the operator role.

In an aspect, the operator role can comprise the manipulation of one or more input hardware devices. As an example, one or more video capture cards can be enabled to capture one or more images. As another example, a local processor can write one or more images through said video capture card to a circular or ring buffer. As another example, one or more images can be written to a queue. As a further example, one or more images can be written to a stack.

In an aspect, a particular texture processing can be associated with the operator role. As an example, an image can be mapped to a screen according to a specified coordinate transformation, wherein inputs are given as parameters to a fragment or pixel shader. As a further example, one or more programmable functions associated with the operator role can be used to modify the traits (e.g., color, z-depth, alpha value) of one or more pixels of a given image. As another example, an image can have background subtraction, background removal, object detection, or similar algorithms applied to it for selective display of a region of the image.

In an aspect, for the operator role, one or more images captured by a local camera and processed by a local processor are rendered with an opacity of substantially one. As an example, one or more images of a local "scene of interest" can be rendered with substantially full opacity. As a further example, one or more images captured by a local camera and processed by a local processor can be rendered with an opacity of less than one, providing a degree of transparency. One or more images captured by a remote camera and processed by a remote processor can be rendered with an opacity of less than 1, thereby providing a degree of transparency. As another example, one or more images of a remote user can be tiled or arranged on the display screen (i.e., picture-in-picture). As a further example, one or more images of a remote user's environment can be tiled or arranged on the display screen.

In an aspect, a "heads up" role can comprise the manipulation of data flow and data presentation. As an example, the heads up role can comprise a particular arrangement of a software pipeline, such as a series of processing elements for which the output of one processing element is the input for the successive processing element. As a further example, images captured by a local camera and processed by a local processor can be merged with images captured by one or more remote cameras and processed by one or more remote processors in a manner that is associated with the heads up role.

In an aspect, the heads up role can comprise processing images captured by one or more local cameras to facilitate display alongside images captured by one or more remote camera and processed by one or more remote processors. As an example, the local and remote images can be tiled. As another example, one or more local images can be rendered in a manner utilizing a plurality of the screen, with one or more remote images displayed in a relatively smaller window. As a further example, one or more remote images can be rendered in a manner utilizing a majority of the screen, with one or more local images displayed in a relatively smaller window. Other roles and associated processing can be used.

In an aspect, processing of images can be implemented via a local processor prior to transmission to a remote processor. For example image processing can occur at a local processor prior to transmission. As a further example, role designation can be implemented as an implicit role designation that occurs when a user of a system is processing images versus a user that is merely receiving processed images.

Figure 4A:
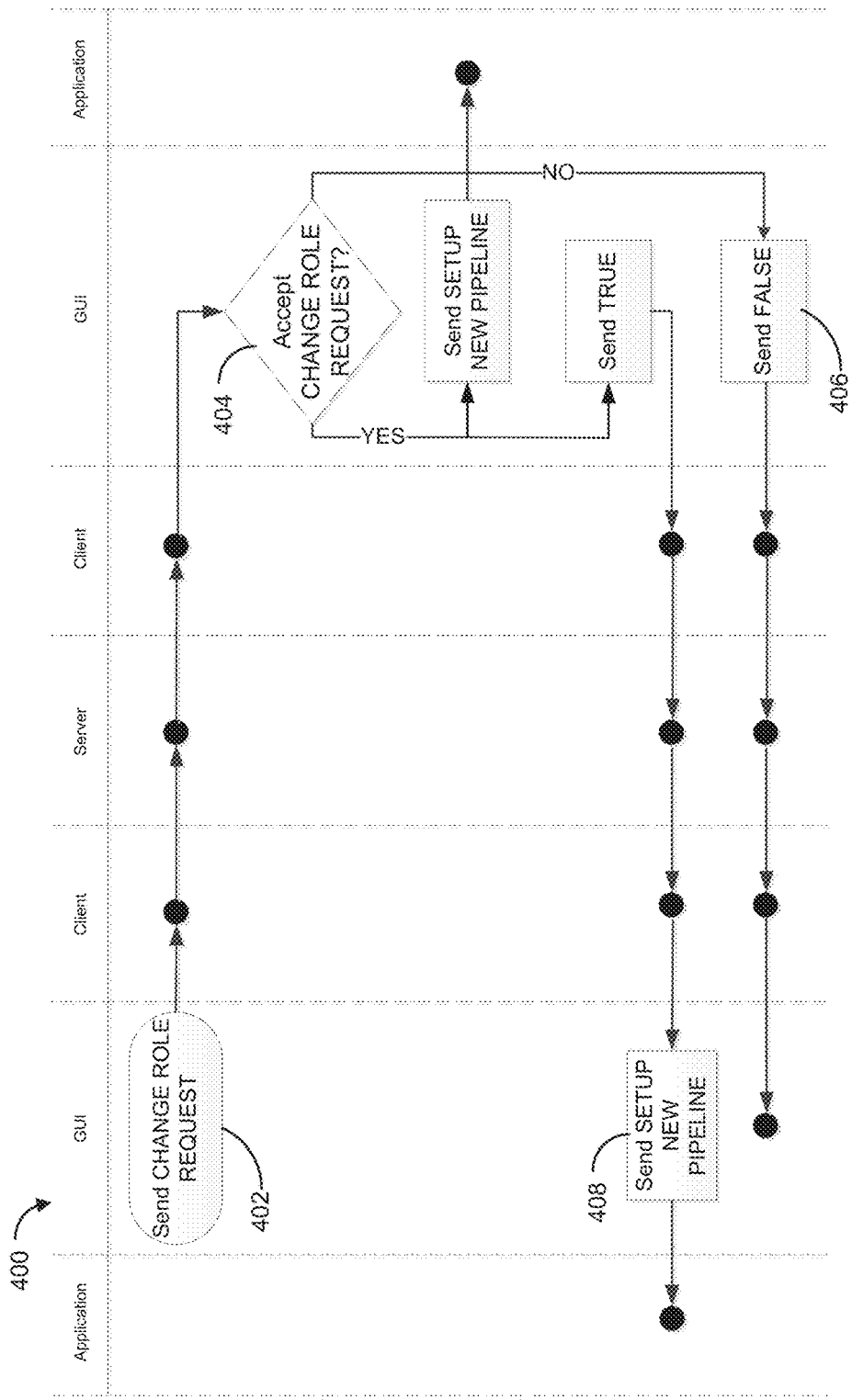
FIG. 4A illustrates an exemplary process performed by the system of FIG. 3.

FIG. 4A illustrates exemplary process 400 that can be performed with at least one of the processors 310, 312. Other processor and/or computing devices can be used to perform the process 400. In step 402, a request for a role change or role designation can be transmitted/received. In an aspect, a button push on a graphical user interface initiates an event which facilitates transmission of a "role change request" from the graphical user interface of a first application to the graphical user interface of one or more other applications. As an example, the role change request can comprise a designation or specification of the role a local user desires the local application to assume. As an example, the role change request can be a communication comprising the desired role as a string literal. As another example, the role change request could be a communication comprising the desired role as an integer mapped to a string in a table of a database.

In an aspect, triggering the transmission/receipt of a role change request can be facilitated by one or more logical or physical events. As an example, an event can be triggered via an input from a user. As further examples, an event can be triggered via gesture recognition, speech recognition, the triggering of an accelerometer, a swipe, a pinch, or a touch, or a combination thereof.

In an aspect, the role change request can be transmitted to a local client program, which can be defined as a computer application or computer program that communicates with a server to access a service. As an example, the local client program can transmit the request to a server over a network. The local client program can transmit the request to a server running on the same computer, avoiding having to traverse a network. The server can be comprised as a computer hardware or computer software that provides access to a service for a client program. As a further example, the server can transmit the role change request to one or more client programs as specified by the request. In an aspect, each client program can transmit the request to a remote graphical user interface of a remote application.

In step 404, when the graphical user interface receives the request, one or more conditional statements (e.g., IF-THEN statements) can be executed to determine whether to accept the request. In an aspect, a sequence of conditional statements can be executed by a local processor to determine whether to accept the change role request.

In an aspect, the local processor can perform a check to determine whether a role corresponding to the role specified in the change role request can be located and/or generated. As an example, if no corresponding role is located, a negative (i.e., FALSE) response can be transmitted to a local client, at step 406. As an example, the local client can transmit the response to a central server. The central server can transmit the response to one or more remote clients. The remote clients can present the response to corresponding graphical user interfaces. As a further example, if a corresponding role is located, the role (and the associated functionality) can be used to control the presentation of images via one or more displays. In an aspect, an identifier such as a character or string can be used to identify one or more roles, at step 408. As an example, the identifier can be used to associate particular processing paths and/or presentation configurations with one or more role designations. Accordingly, role designations can be selected, processed, located, manipulated, and the like based upon the identifier associated therewith.

In an aspect, a processor can perform a validation check to determine whether the local application is already in the corresponding role. If true, the processor can initiate the sending of an affirmative response (i.e., TRUE) from the local graphical user interface of the local application to the remote graphical user interface of one or more remote applications. If the corresponding role is not equal to the local application's current role, the current role of the local application can be reassigned or designated to the corresponding role. As such, the arrangement, organization, and/or presentation of a graphical user interface as displayed to one or more users can be modified. As an example, a software pipeline associated with the designated role can be configured.

In an aspect, pseudocode for updating a current role presented via an interface can comprise:

```
IF (corresponding_role_found)
    role ← corresponding_role
    IF (role = current_role)
        SEND true
    ELSE
        current_role ← role
        SEND true
    ENDIF
ELSE
    SEND false
ENDIF
```

FIG. 4B illustrates an exemplary schematic of a multi-reality session. In an aspect, a first user 412 at a first location 414 having a field of interest 416 can be in communication with a second user 418 at a second location 420. As an example, the first user 412 can be in the operator role, while the second user 418 can be in the helper role. As such, the field of interest 416 can be shared between the first user 412 and the second user 418. As a further example, the field of interest 416 can be configured to present images in a first configuration associated with the first user 412 designated as the operator role. Following a role change, the first user 412 can assume the helper role, while the second user 418 can assume the operator role. As such, the field of interest 416 can be shared between the first user 412 and the second user 418 and can be updated to present images in a second configuration based on the second user 418 designated as the operator role.

In an aspect, processing of images can be implemented via a local processor prior to transmission to a remote processor. For example image compositing can occur at a local processor prior to transmission. As such, images and/or video received by a remote processor does not require compositing and can be accepted by a codec. As a further example, role designation can be implemented as an implicit role designation that occurs when a user of a system is compositing images versus a user that is merely receiving processed images.

FIG. 4C illustrates an exemplary rendering of the field of interest 416 configured to illustrate the first user 412 designated in the operator role. In an aspect, FIG. 4C illustrates the field of interest 416 from the perspective of the first user 412. In another aspect, one or more video capture cards can be enabled to capture one or more images of a local field of interest (e.g., prosthetic knee). The images of the field of interest 416 can be rendered with an opacity of substantially one. Images of a hand 420 of the first user 412 and a hand 422 of the second user 418 can be rendered with an opacity of less than one, while images of a face 424 of the second user 418 can be tiled or arranged on the display with an opacity of substantially one.

Figure 4D:
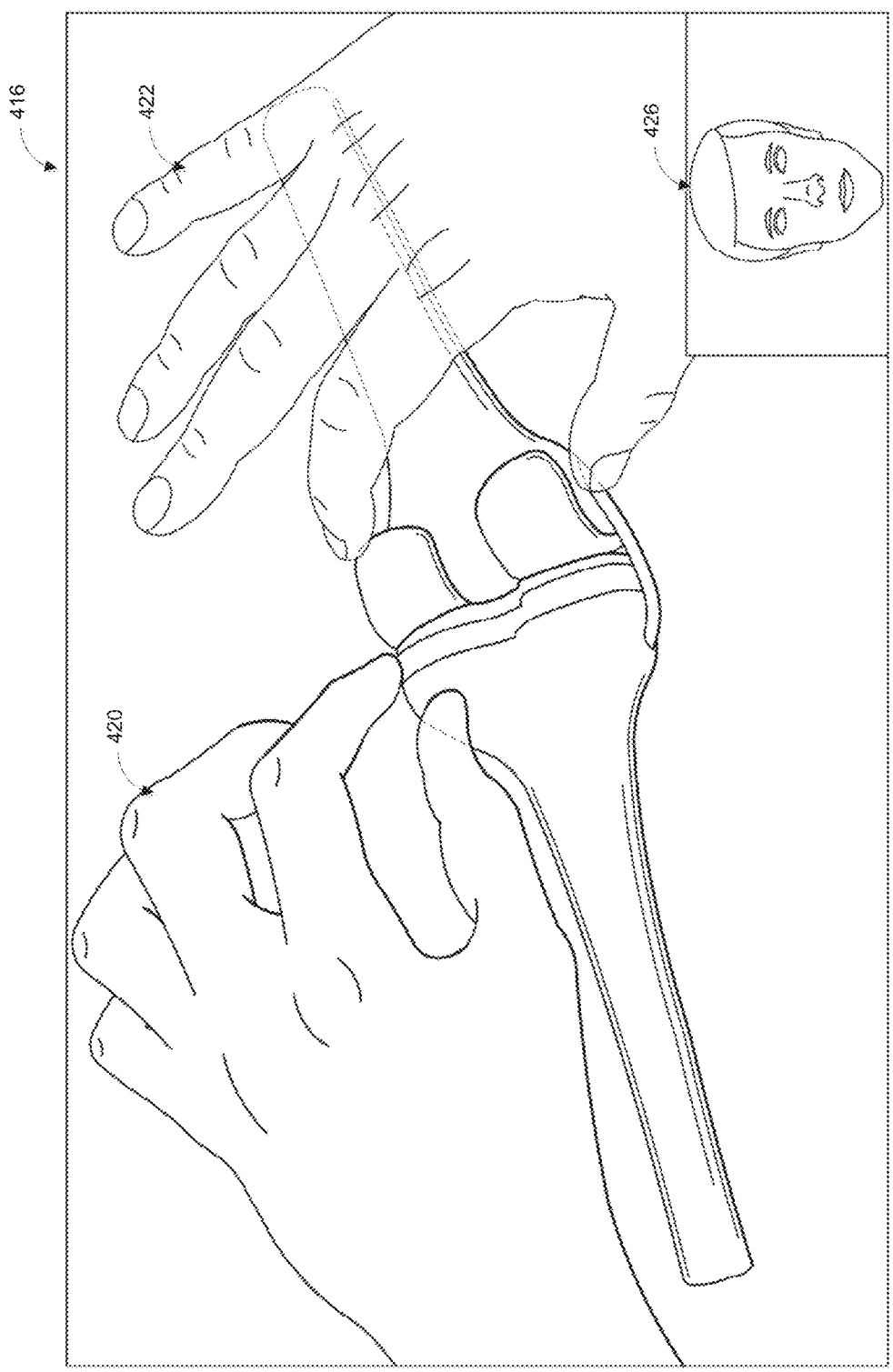
FIG. 4D illustrates an exemplary user interface.

FIG. 4D illustrates an exemplary rendering of the field of interest 416 configured to illustrate the second user 418 designated in the helper role. In an aspect, FIG. 4D illustrates the field of interest 416 from the perspective of the second user 418. The images of the field of interest 416 can be rendered with an opacity of substantially one. Images of the hand 420 of the first user 412 and the hand 422 of the second user 418 can be rendered with an opacity of less than one, while images of the face 426 of the first user 412 can be tiled or arranged on the display with an opacity of substantially one.

In an aspect, a selection of a graphical button rendered on a touch-sensitive display can be used to initiate a role change request. As an example, the graphical button push can initiate the transmission of a role change request from a graphical user interface rendered by a first processor to a graphical user interface rendered by a second processor. As a further example, the graphical button can specify a role that the second user desires to assume.

In an aspect, FIG. 4E illustrates an exemplary rendering of a graphical user interface 428 to one or more users. One or more graphical buttons 430 can allow a user to make a role designation such as "Operator," "Helper," and/or "Heads Up." A video window 432 can display one or more images. Additional options may be exposed to the user, which can allow further manipulation of the video image in a multi-reality session. As an example, a graphical "blend value" slider 434 can allow a user to determine the relative proportions of real and virtual images viewed. As another example, a graphical "exposure value" slider 436 can allow a user to modulate the exposure properties of a local or remote camera. As a further example, a graphical "telestration" menu 438 can allow a user to perform virtual drawings on top of a video image. A graphical "preferences" button 440 and graphical "end session" button 442 can allow a user to modulate other session parameters and end the current session with a remote user, respectively.

Figure 4F:
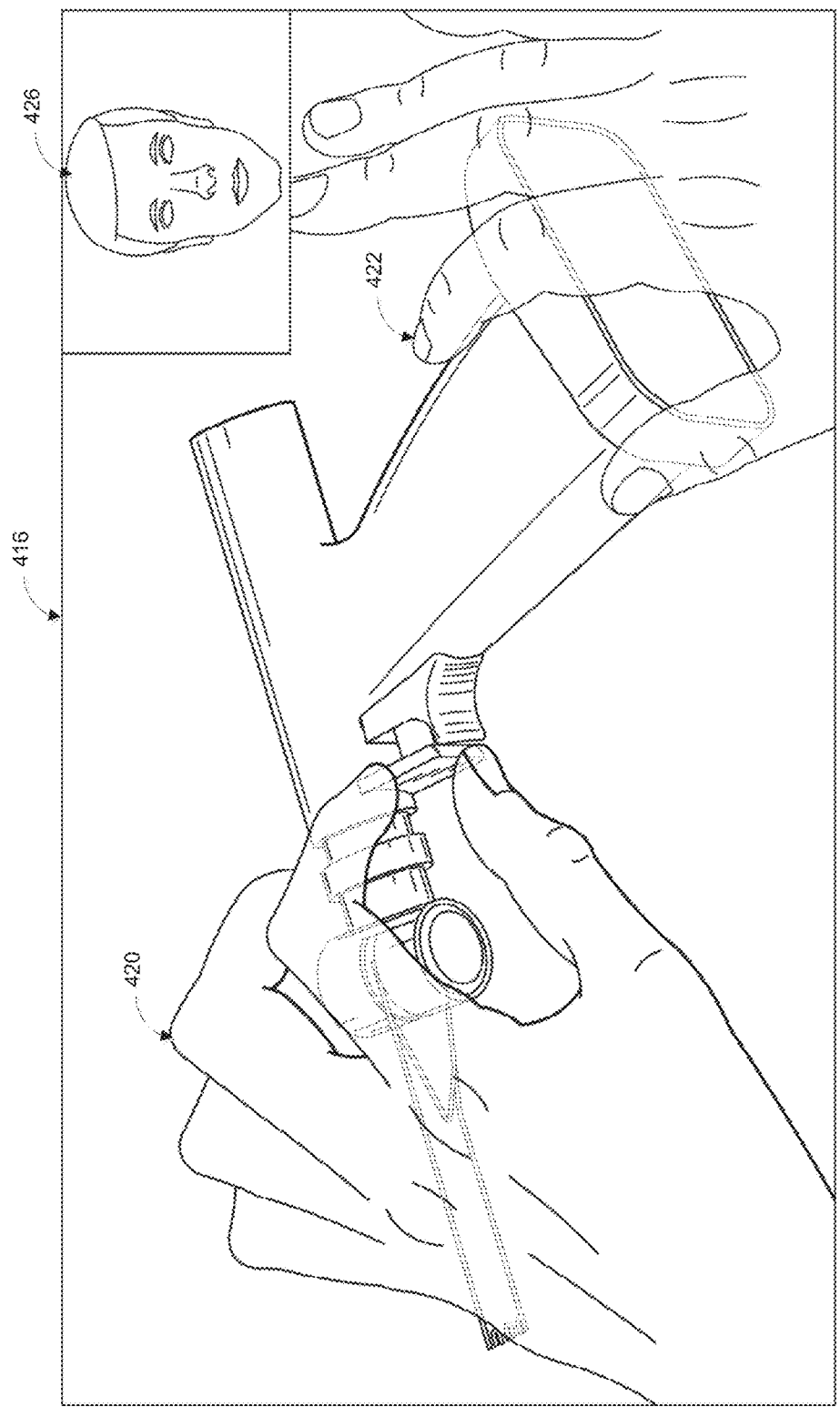
FIG. 4F illustrates an exemplary user interface.

FIG. 4F illustrates an exemplary rendering of the field of interest 416 configured to illustrate the second user 418 designated in the operator role. In an aspect, FIG. 4F illustrates the field of interest 416 from the perspective of the second user 418. In another aspect, one or more video capture cards can be enabled to capture one or more images of a local field of interest (e.g., prosthetic knee). The images of the field of interest 416 can be rendered with an opacity of substantially one. Images of the hand 420 of the first user 412 and the hand 422 of the second user 418 can be rendered with an opacity of less than one, while images of the face 426 of the first user 412 can be tiled or arranged on the display with an opacity of substantially one.

Figure 4G:
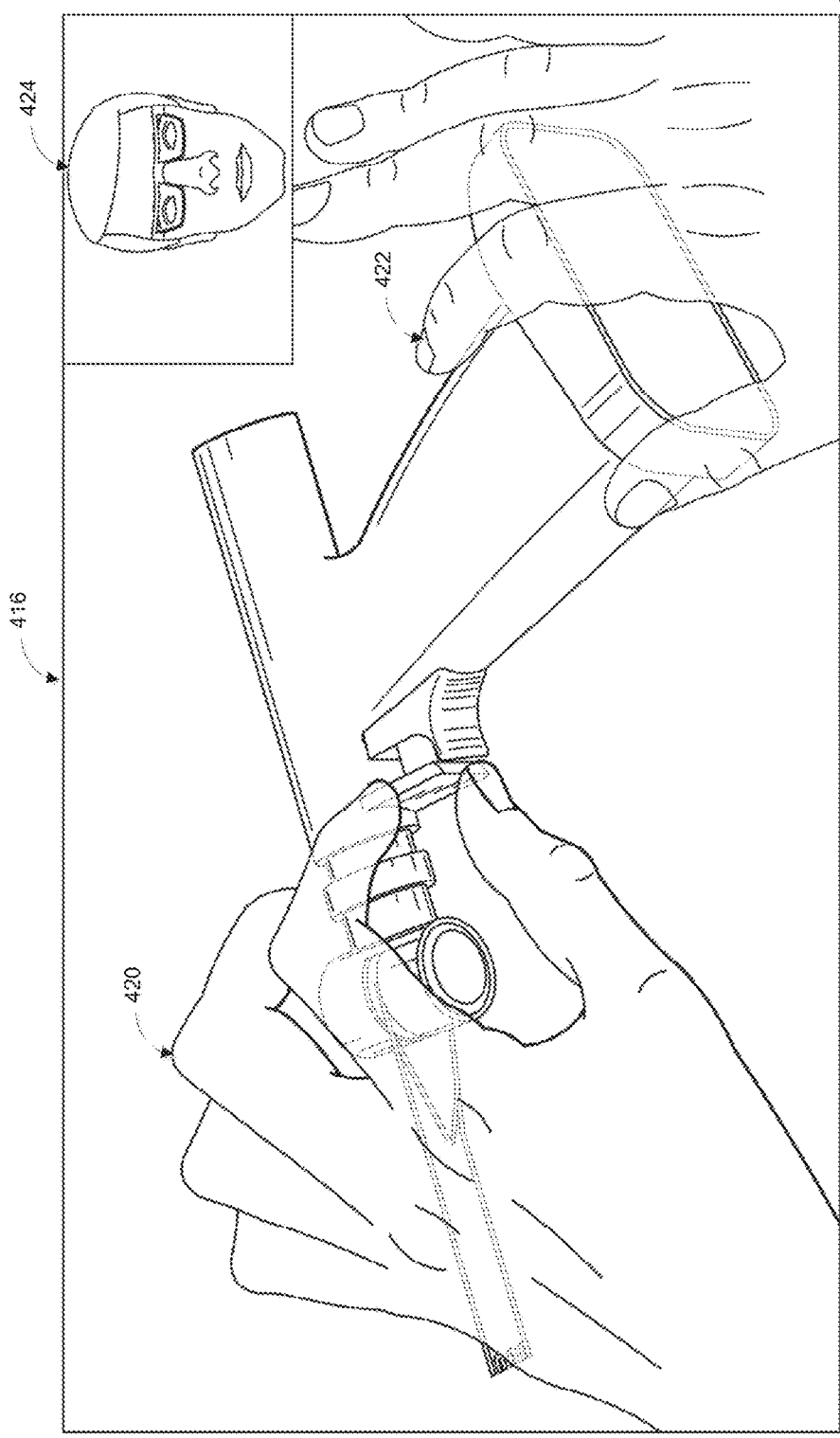
FIG. 4G illustrates an exemplary user interface.

FIG. 4G illustrates an exemplary rendering of the field of interest 416 configured to illustrate the first user 412 designated in the helper role. In an aspect, FIG. 4G illustrates the field of interest 416 from the perspective of the first user 412. The images of the field of interest 416 can be rendered with an opacity of substantially one. Images of the hand 420 of the first user 412 and the hand 422 of the second user 418 can be rendered with an opacity of less than one, while images of the face 424 of the second user 418 can be tiled or arranged on the display with an opacity of substantially one.

Figure 5:
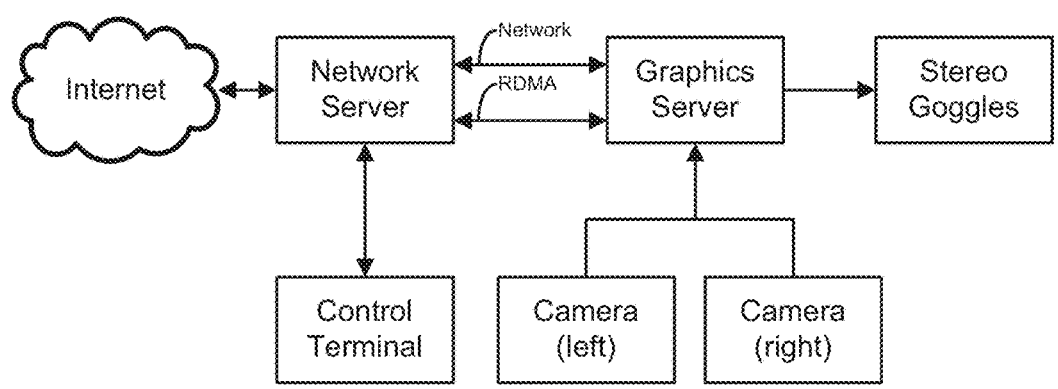
FIG. 5 illustrates an exemplary virtual presence system.

FIG. 5 illustrates an exemplary virtual presence system. One such system can be used by each remote participant that is to join the same session. Each system can communicate with each other through a network connection. For example, remote sites can connect via the Internet. Tasks can be divided amongst a plurality of computers in each system. For example, one computer (a graphics server) can gather images from local cameras and a network server, perform the stereo image composition tasks, and drive a local stereoscopic display system. As a further example, the processor(s) 310 of system 300 can be embodied by the graphics server.

Figure 6:
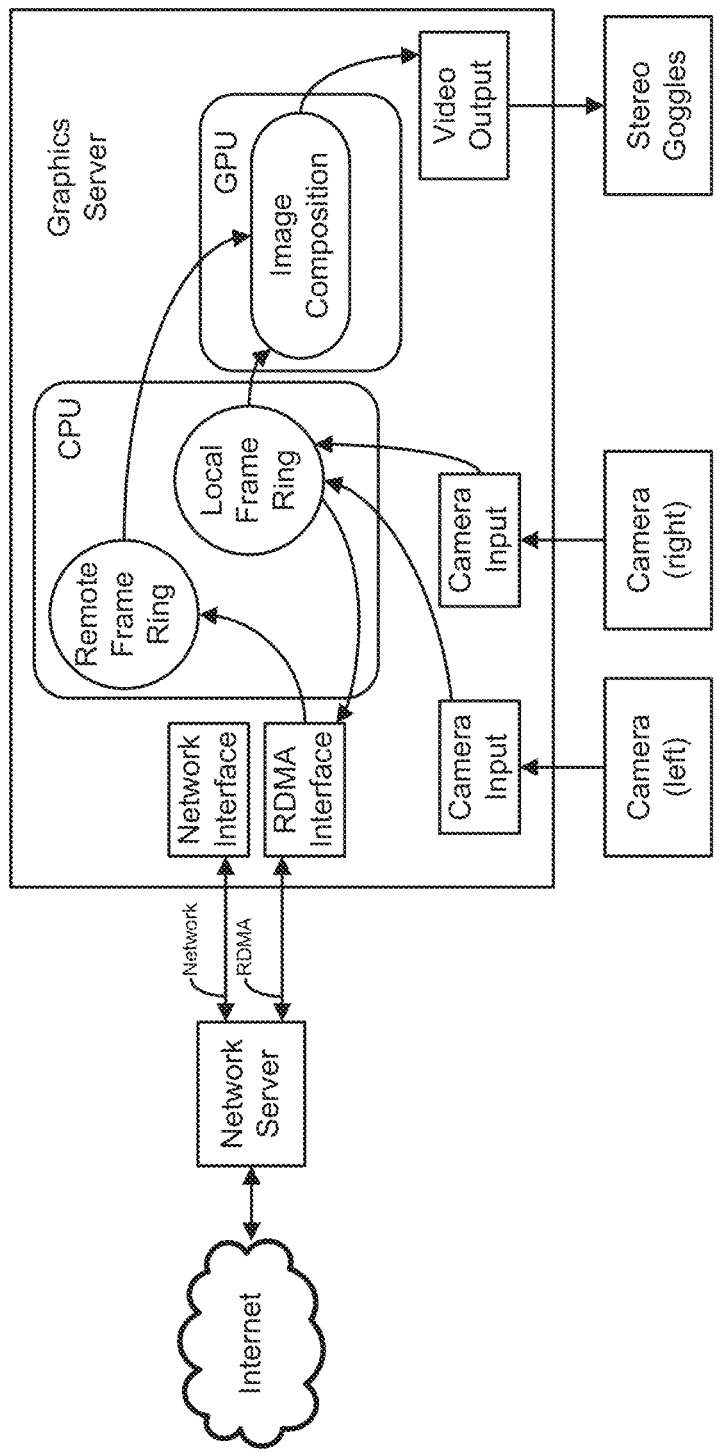
FIG. 6 illustrates exemplary processes performed within a graphics server.

FIG. 6 illustrates exemplary processes that can be performed with the graphics server. Images can be gathered into local data structures (frame rings). Local images can be gathered from a plurality of cameras, for example two cameras. Remote images can be provided by the network server via a high-speed remote direct memory access (RDMA) connection, for example. These images can be combined so that the remote user and the local user can be seen in the same scene (as in FIG. 3). This composite result can be transmitted to a local stereoscopic display system. A second computer can act as the network server, which can perform network encoding/decoding tasks as well as depth map generation, for example.

Figure 7:
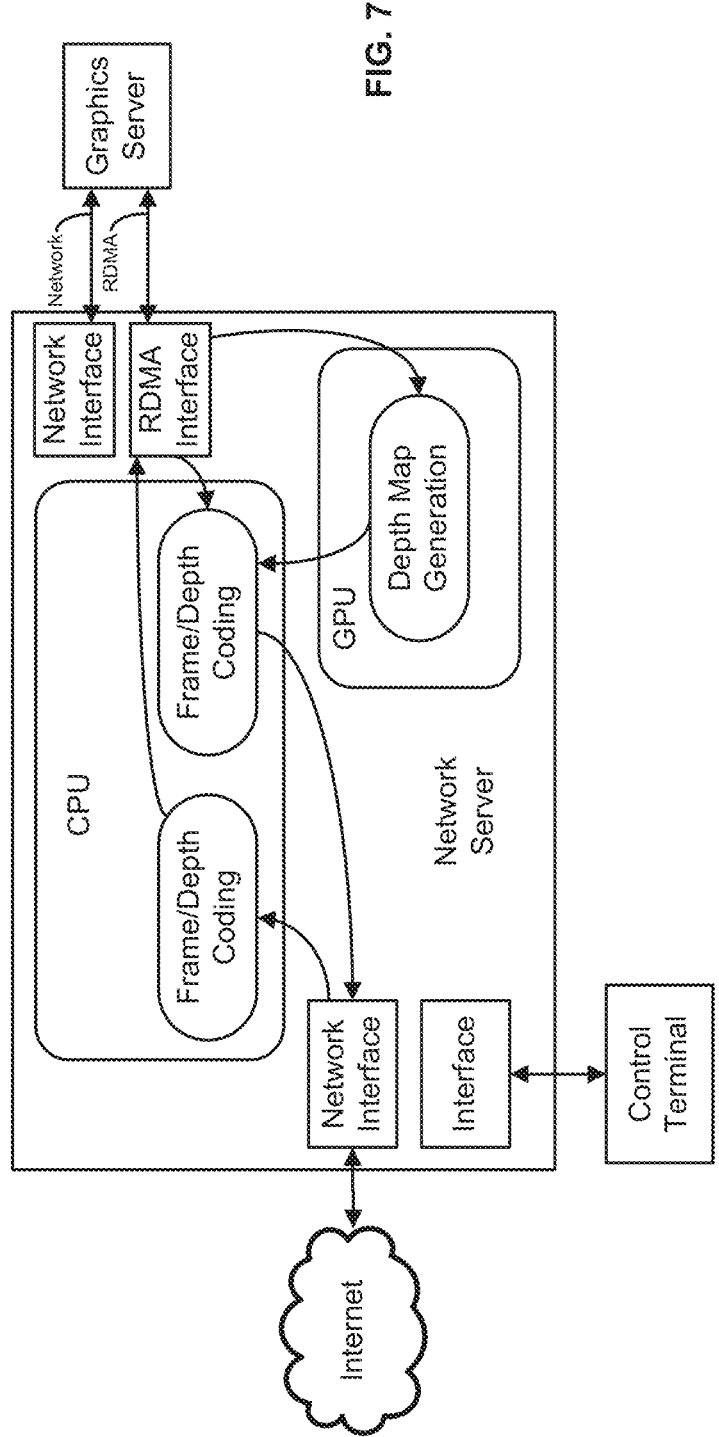
FIG. 7 illustrates exemplary processes performed within a network server.

FIG. 7 illustrates exemplary processes that can be performed with the network server. Local images gathered from the graphics server via the RDMA connection can be analyzed and mapped with depth information, encoded for efficient network transmission, and sent to an external network connection to be received by a corresponding network server at the remote site. Simultaneously, encoded images and depth maps can be received from the remote site, decoded, and provided to the local graphics server via the RDMA connection.

The system can be user-controlled by a control terminal connected to the network server; the user can then access and control the graphics server via the dedicated network connection to the network server.

Parameters of virtual interactive presence can be configured depending on the system used. Configurable parameters include, but are not limited to, size of virtual elements, presence of virtual elements (opaque, translucent, etc.), time of virtual presence (time can be configured to be delayed, slowed, increased, etc.), superimposition of elements such that any combination of virtual and real can be superimposed and/or 'fitted' over one another, and the like.

Figure 8:
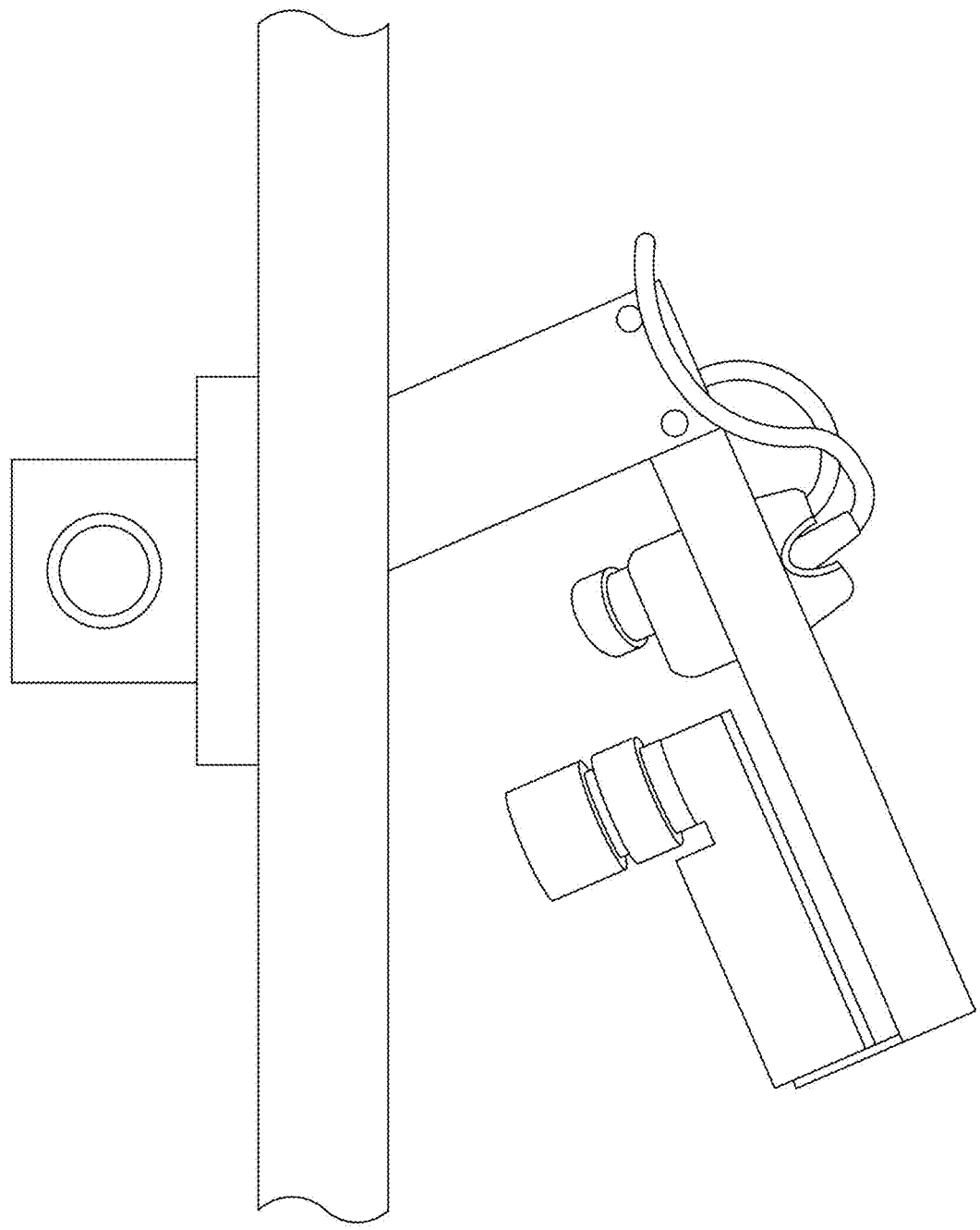
FIG. 8 illustrates a side view of an exemplary VIP display.
Figure 9:
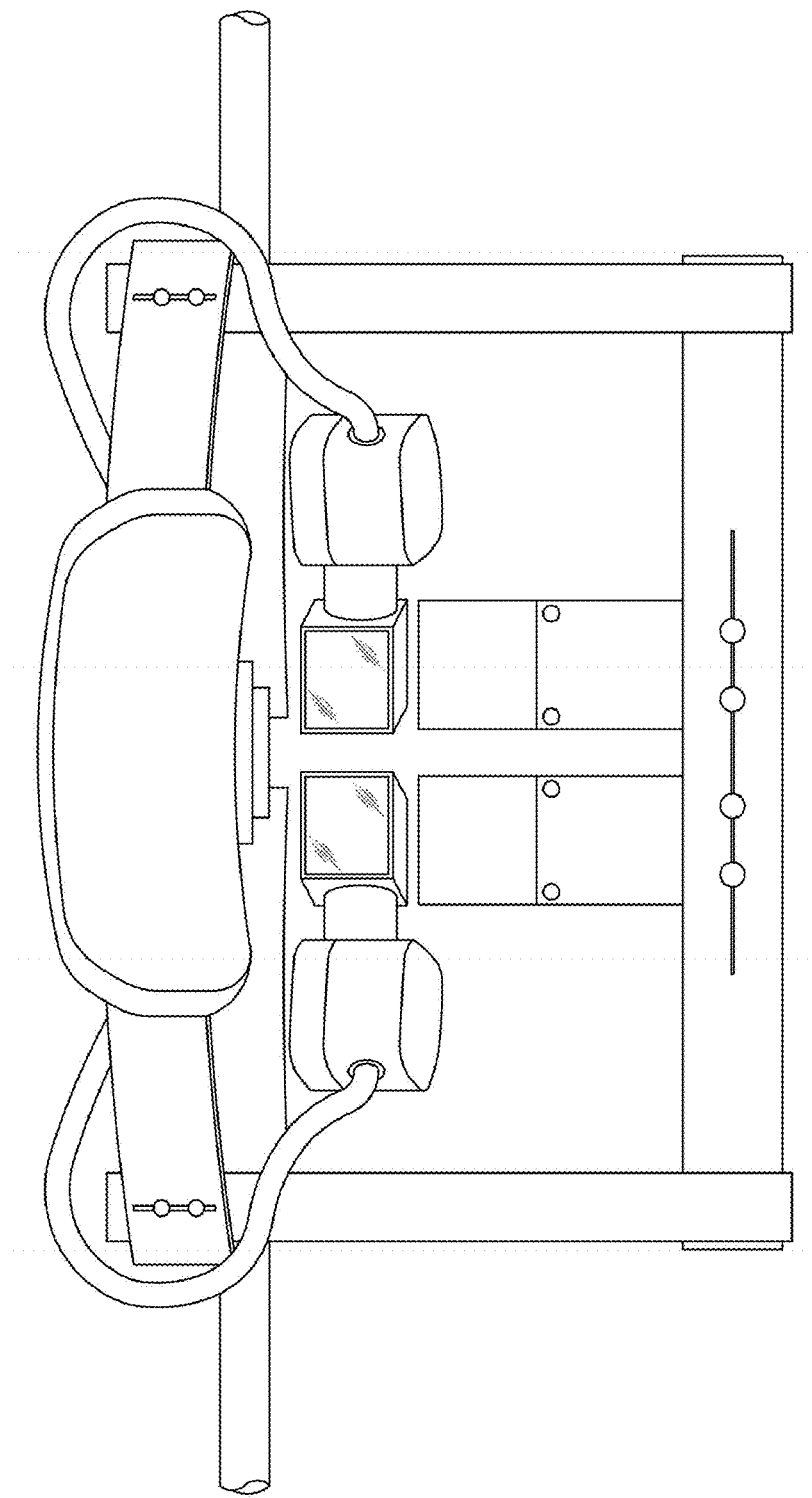
FIG. 9 illustrates a user's view of an exemplary VIP display.
Figure 10:
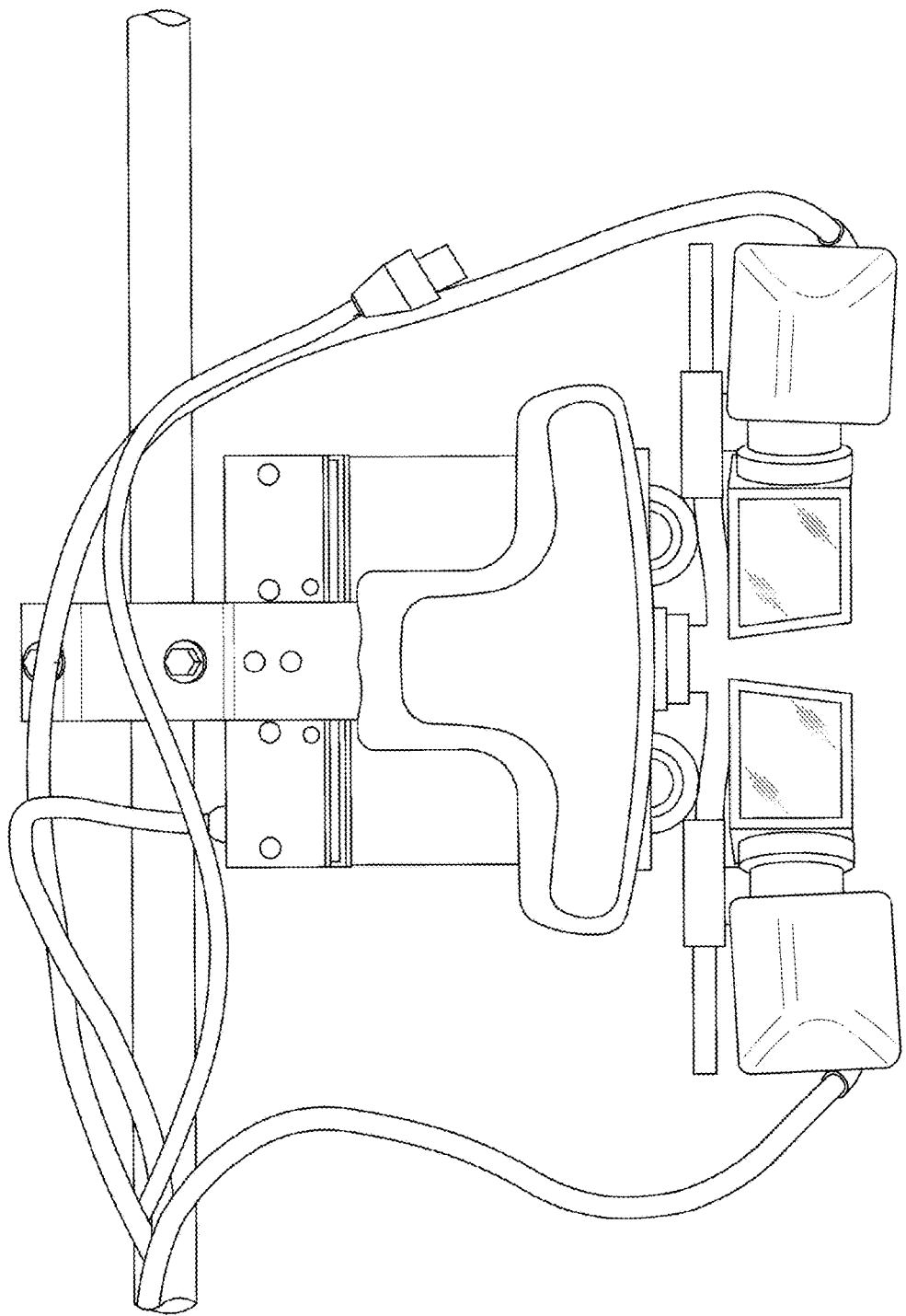
FIG. 10 illustrates a user's view of an exemplary VIP display.

FIG. 8 illustrates a side view of an exemplary VIP display. FIG. 9 illustrates a user's view of an exemplary VIP display. FIG. 10 illustrates a user's view of an exemplary VIP display.

As used herein, a "local" field of interest can refer to a local physical field and local user, thus making every other field remote. Each field can be local to its local physical user, but remote to other users. The composite of the fields can be a common field of interest. This is distinct from common "virtual worlds" in that there can be components of "real" within the local rendering of the common field of interest and interactions can be between actual video (and other) renderings of physical objects and not just graphic avatars representing users and objects. The methods and systems provided allow for virtual interactive presence to modify/optimize a physical domain by the interplay of real and virtual.

Figure 11:
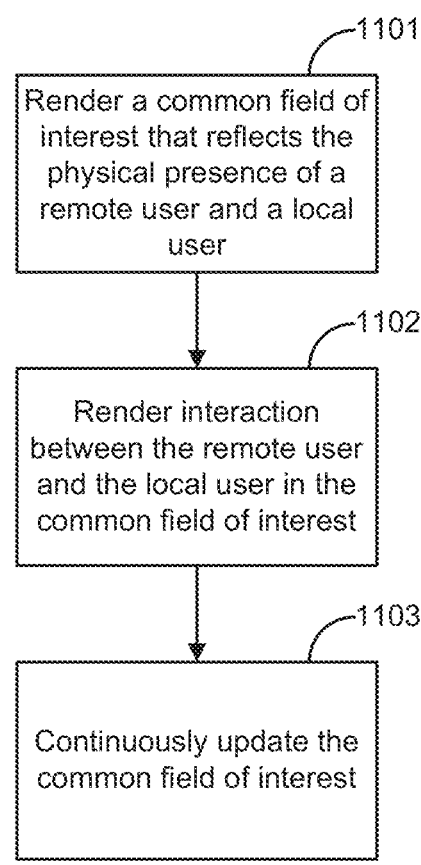
FIG. 11 illustrates an exemplary method.

In an aspect, illustrated in FIG. 11, provided are methods for virtual interactive presence comprising rendering a common field of interest that reflects the physical presence of a remote user and a local user at 1101, rendering interaction between the remote user and the local user in the common field of interest at 1102, and continuously updating the common field of interest such that the presence of the remote user is rendered in real time to the local user and the presence of the local user is rendered in real time to the remote user at 1103.

The common field of interest can be rendered such that the remote user experiences the common field of interest similarly to the local user. The local user can experience the remote user's physical presence in a manner that enables continuous interaction in the common field of interest with the remote user. The methods can further comprise rendering the physical presence of a local object in the common field and rendering interaction between the local user and the local object in the common field. The methods can further comprise rendering the physical presence of a local object in the common field of interest and rendering interaction between the remote user and the local object in the common field of interest.

Figure 12:
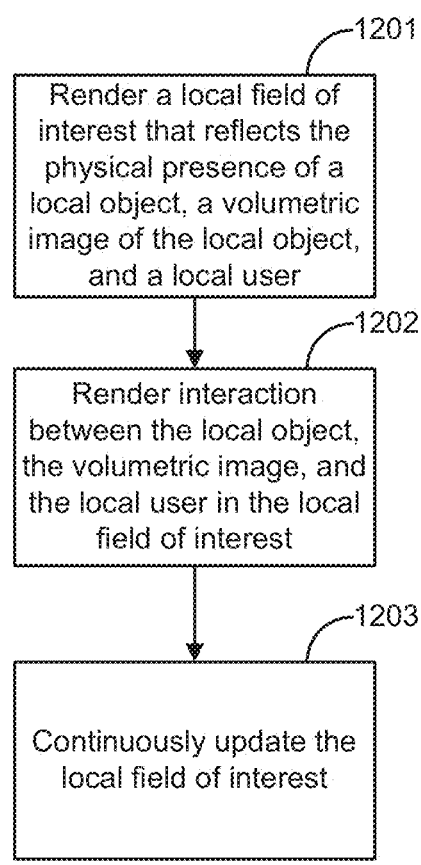
FIG. 12 illustrates another exemplary method.

In another aspect, illustrated in FIG. 12, provided are methods for virtual interactive presence comprising rendering a local field of interest that reflects the physical presence of a local object, a volumetric image of the local object, and a local user at 1201, rendering interaction between the local object, the volumetric image, and the local user in the local field of interest at 1202, and continuously updating the local field of interest such that the presence of the local object and the volumetric image of the local object is rendered in real time to the local user at 1203.

The local object can be, for example, a patient and the volumetric image of the local object can be, for example, a medical image of a part of the patient. However, the local object can be any object of interest and the image of the local object can be any accurate rendering of that object. For example, could be an automobile engine and a 3D graphic of the engine, etc.

The medical image can be, for example, one of, an x-ray image, an MRI image, or a CT image. The methods can further comprise superimposing, by the local user, the volumetric image onto the local object. The superimposition can be performed automatically by a computer.

The methods can further comprise adjusting, by the local user, a property of the volumetric image. The property can be one or more of transparency, spatial location, and scale.

The methods can further comprise rendering a local tool in the local field of interest. The methods can further comprise rendering the local tool in accurate spatial relation to the rendering of the local object. The tool can be any type of tool, for example, a surgical tool.

In another aspect, provided are systems for virtual presence, comprising a virtual presence display, configured for displaying a common field of interest, a local sensor, configured for obtaining local virtual presence data, a network interface, configured for transmitting local virtual presence data and receiving remote virtual presence data, and a processor, coupled to the virtual presence display, the local sensor, and the network interface, wherein the processor is configured to perform steps comprising, rendering a common field of interest that reflects the physical presence of a remote user and a local user based on the local virtual presence data and the remote virtual presence data, rendering interaction between the remote user and the local user in the common field of interest, continuously updating the common field of interest such that the presence of the remote user is rendered in real time to the local user and the presence of the local user is rendered in real time to the remote user, and outputting the common field of interest to the virtual presence display.

The virtual presence display can be one or more of a stereoscopic display, a monoscopic display (such as a CRT, LCD, etc.), and the like. The sensor can be one or more of a camera, an infrared sensor, a depth scan sensor, and the like. The common field of interest can be rendered such that the remote user experiences the common field of interest similarly to the local user. The local user can experience the remote user's physical presence in a manner that enables continuous interaction in the common field of interest with the remote user.

The processor can be further configured to perform steps comprising rendering the physical presence of a local object in the common field of interest and rendering interaction between the local user and the local object in the common field of interest.

The processor can be further configured to perform steps comprising rendering the physical presence of a local object in the common field of interest and rendering interaction between the remote user and the local object in the common field of interest.

Further provided are systems for virtual presence, comprising a virtual presence display, configured for displaying a local field of interest, a local sensor, configured for obtaining local virtual presence data, a processor, coupled to the virtual presence display and the local sensor, wherein the processor is configured to perform steps comprising, rendering a local field of interest that reflects the physical presence of a local object and a local user based on the local virtual presence data and a volumetric image of the local object, rendering interaction between the local object, the volumetric image, and the local user in the local field of interest, continuously updating the local field of interest such that the presence of the local object and the volumetric image of the local object is rendered in real time to the local user, and outputting the local field of interest to the virtual presence display.

The virtual presence display can be one or more of a stereoscopic display, a monoscopic display (such as a CRT, LCD, etc.), and the like. The sensor can be one or more of a camera, an infrared sensor, a depth scan sensor, and the like.

The local object can be, for example, a patient and the volumetric image of the local object can be, for example, a medical image of a part of the patient. The medical image can be, for example, one of an x-ray image, an MRI image, or a CT image. However, the local object can be any object of interest and the image of the local object can be any accurate rendering of that object. For example, could be an automobile engine and a 3D graphic of the engine, etc.

The processor can be further configured to perform steps comprising superimposing, by the local user, the volumetric image onto the local object. The processor can be further configured to perform steps comprising adjusting, by the local user, a property of the volumetric image. The property can be one or more of transparency, spatial location, and scale.

The processor can be further configured to perform steps comprising rendering a local tool in the local field of interest. The processor can be further configured to perform steps comprising rendering the local tool in accurate spatial relation to the rendered local object.

The disclosed methods and systems can have broad applications. For example, surgery, gaming, mechanics, munitions, battle field presence, instructional efforts (training) and/or any other situation where interaction is part of the scenario.

Also disclosed are methods and systems that enable a remote expert to be virtually present within a local surgical field. Virtual interactive presence can be used to enable two surgeons remote from each other to interactively perform a surgical procedure. The methods and system enable two or more operators to be virtually present, and interactive, within the same real operative field, thus supporting remote assistance and exporting surgical expertise.

The methods and systems can also be used to superimpose imaging data of the operative anatomy onto the anatomy itself for guidance and orientation (augmented reality). The methods and systems can be used for training of students. The methods and systems augment and enhance the field of robotics by virtually bringing an expert into the robotic field to guide the robot operator. The methods and systems are applicable to endoscopic procedures by inserting the expert's hands directly into the endoscopic field for guidance. The methods and systems expand remote surgery by providing the assistance of a remote expert to an actual local surgeon, whose basic skills can handle emergencies, and who will learn from the virtual interaction. The methods and systems can be used at trauma sites and other medical environments. The methods and systems can be used to provide remote assistance in other areas such as engineering, construction, architecture, and the like. The methods and systems disclosed can be used to transmit expertise to a remote 'site of need', merge contemporary imaging directly into the surgical field, and train surgical students An exemplary remote surgical assistance system for transmitting surgical maneuvers of a local expert to a remote surgeon for the purpose of guiding/assisting the remote surgeon is illustrated in FIG. 13. The remote surgical field can be viewed by the remote surgeon with a binocular video system. The video system can show the field with his hands and instruments performing the procedure. The viewing system can be referred to as a surgical videoscope.

The binocular video rendering of the remote field can be transmitted to the local expert), who can view the (now virtual) stereoscopic rendering of the procedure through a second surgical videoscope system. The local expert can insert his hands into the virtual field, thus seeing his real hands within the virtual field.

The video image of the local expert's hands can be transmitted back to the remote surgeon's surgical videoscope system superimposed into the real field. The remote surgeon can then see the expert's virtual hands within his surgical field in a spatially/anatomically relevant context. With this system, the local expert can use his hands to show the remote surgeon how to perform the case.

Exemplary elements of the system can comprise a remote station where the remote surgeon can perform the operative procedure, a remote surgical videoscope system comprised of, for example, a fixed stereoscopic videoscope that may resemble a mounted microscope. This apparatus can be used by the remote surgeon to view the operative field. Any other type of suitable VIP display can be used. The system can project the binocular video image to a similar local surgical videoscope at a local station. The local surgical videoscope can receive the binocular video image of the remote procedure and allow the local expert to view it. The local videoscope can view the local surgeons hands as they move within the virtual remote field as viewed through the local videoscope. The local videoscope can then transmit the local expert's hands back to the remote videoscope so that the remote surgeon can see the expert's virtual hands within the real field.

With this system, the local expert can show the remote surgeon the appropriate maneuvers that result in successful completion of the case. The remote surgeon can have a basic skill set to carry out the new procedure. Therefore, the local expert can simply demonstrates to the remote surgeon new ways to apply the skill set. This system does not have to supplant the remote surgeon, but can be used to enhance his/her capability. The remote surgeon can be on hand to rapidly deal with any emergencies. Time delay is minimized because the remote surgeon can use his/her own hands to perform the task, eliminating the need for the local expert to manipulate remote robotic apparatuses.

Also disclosed are methods and systems for merging contemporary medical imaging onto an operative field. A volume image can be obtained of the operative field. For example, a volume MRI of the head, prior to the surgical procedure. The image data can be reconstructed into a three dimensional rendering of the anatomy. This rendering can be transmitted to the surgical videoscope that will be used to view the operative field. Through the videoscope, the surgeon can view this 3D rendering in a translucent manner superimposed onto the surgical field. In this case, the surgeon would see a rendered head superimposed on the real head. Using software tools in the surgical videoscope interface, the surgeon can rotate and scale the rendered image until it "fits" the real head. The videoscope system can allow the surgeon to differentially fade the rendered head and real head so that the surgeon can "look into" the real head and plan the surgery.

Exemplary elements of the system can comprise a surgical videoscope viewing system through which the surgeon views the surgical field. A computer for reconstruction of a volume-acquired MRI/CT (or other) image with sufficient resolution to enable matching it to the real surgical anatomy. The volume rendered image can be displayed through the videoscope system so that the surgeon can see it stereoscopically. A software interface can enable the surgeon to vary the translucency of the rendered and real anatomy so that the rendered anatomy can be superimposed onto the real anatomy. The surgeon can "open up" the rendered anatomy to view any/all internal details of the image as they relate to the real anatomy. Surgical tools can be spatially registered to the rendered anatomy so that behavior can be tracked and applied to the image.

As shown in FIG. 14, an example of such a task is placing small objects inside a jar of dark gelatin so that they are not visible to the surgeon. The task is for the surgeon to use a long forceps to reach into the gelatin and touch or grasp the objects. The Surgical Videoscope system can obtain a volume scan of the gelatin jar and render the jar in three dimensions and display a binocular rendering through the videoscope. The surgeon can view the rendering and the real jar through the scope system and fit the rendered jar onto the real jar. By differentially adjusting translucency, the surgeon can reach into the real jar with a forceps and grasp a selected object, while avoiding other designated objects.

The grasping instrument can be spatially registered onto the volumetric rendering of the surgical field, thereby allowing a graphic of the tool to be displayed on the rendering of the surgical field in appropriate anatomic orientation. This can provide enhanced guidance. This can be implemented by touching designated landmarks on the real object (jar) with a digitizer that communicates with the image rendering system, thus defining the object/probe relationship. Because the object (jar) is registered to the image of the jar by superimposition, a graphic of the probe can be displayed in relation to the image of the jar enabling virtual surgery.

There are many situations in which the present system can be used. For example, remote surgery, medical training, and tele-medicine, which can be used for third world countries or in a military situation. Surgeons remotely located from patients can assist other surgeons near the patient, can assist medics near the patient, and can perform surgical operations when coupled to a robotic surgery system. Other examples include, augmented or enhanced surgery—normal surgery using virtual environments, an example of which is endoscopic surgery. Surgical procedures can also be simulated. Surgeons located remote from each other may plan and practice a procedure before carrying out the operation on a real patient.

Other applications include the preparation of patient before surgery, medical therapy, preventative medicine, exposure therapy, reducing phobias, training people with disabilities and skill enhancement, and the like.

The viewer then views the projection through passive stereoscopic polarized glasses (similar to sunglasses) that route the left-eye image to the left eye, and the right-eye image to the right eye. This provides an illusion of stereopsis when the correctly-offset images are properly rendered by the software. The system can be replaced by other types of stereoscopic displays with no functional detriment to the system. The stereoscopic display can comprise at least two display projectors fitted with polarizing lenses, a back-projection screen material that maintains light polarization upon diffusion, special glasses that restrict each eye to see only light of a particular polarization, and the viewer. The image to be viewed can be rendered with two slightly different view transformations, reflecting the different locations of the ideal viewer's two eyes. One projector displays the image rendered for the left eye's position, and the other projector displays the image rendered for the right eye's position. The glasses restrict the light so that the left eye sees only the image rendered for it, and the right eye sees only the image rendered for it. The viewer, presented with a reasonable stereoscopic image, will perceive depth.

Figure 15:
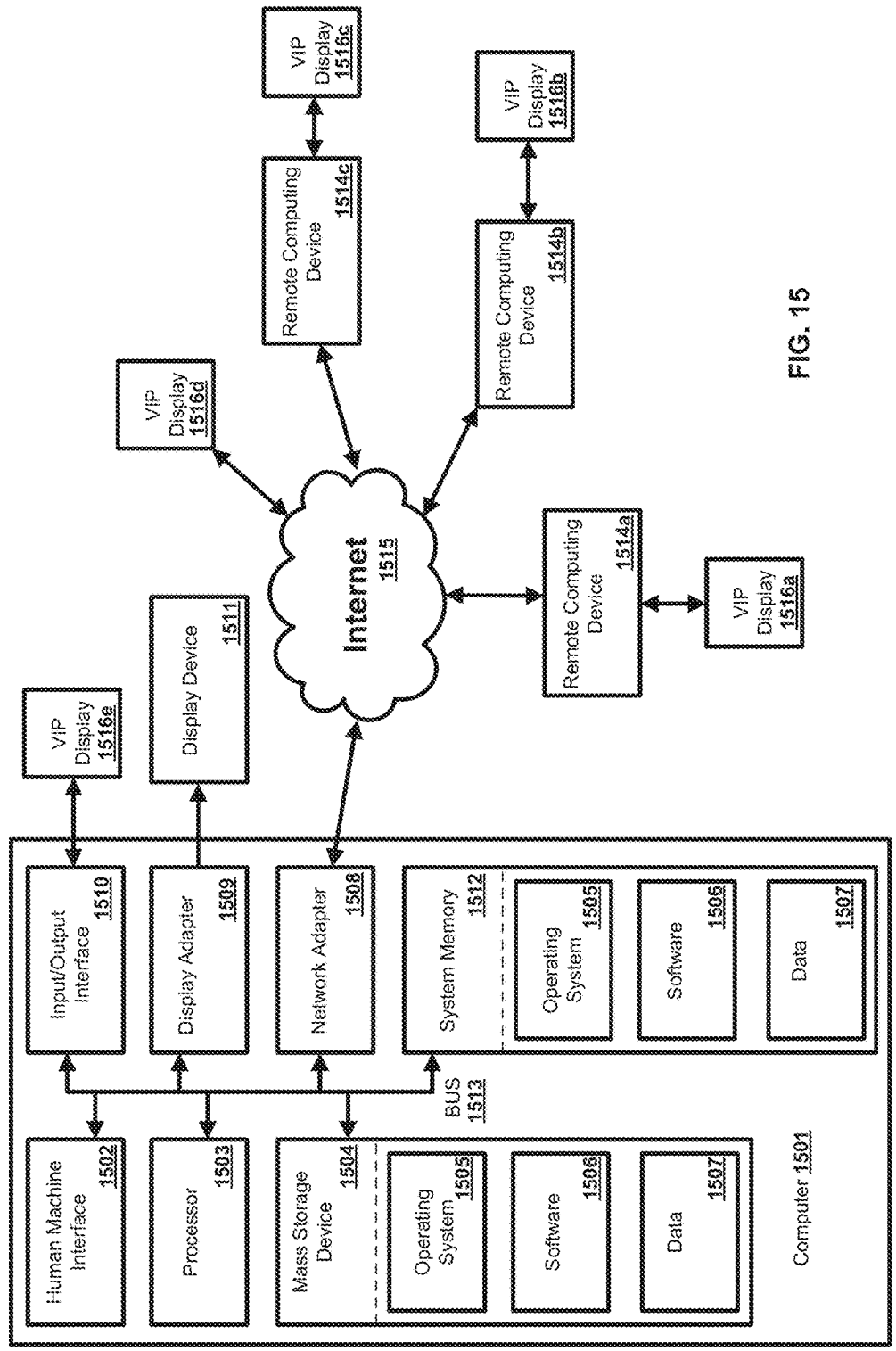
FIG. 15 illustrates an exemplary operational environment.

FIG. 15 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The methods can be operational with numerous other general purpose or special purpose computing system environments or configurations. Examples of well known computing systems, environments, and/or configurations that may be suitable for use with the system and method include, but are not limited to, personal computers, server computers, laptop devices, and multiprocessor systems. Additional examples include set top boxes, programmable consumer electronics, network PCs, minicomputers, mainframe computers, distributed computing environments that include any of the above systems or devices, and the like.

The methods may be described in the general context of computer instructions, such as program modules, being executed by a computer. Generally, program modules include routines, programs, objects, components, data structures, etc. that perform particular tasks or implement particular abstract data types. The system and method may also be practiced in distributed computing environments where tasks are performed by remote processing devices that are linked through a communications network. In a distributed computing environment, program modules may be located in both local and remote computer storage media, including memory storage devices.

The methods disclosed herein can be implemented via one or more general-purpose computing devices in the form of a computer 1501. The components of the computer 1501 can include, but are not limited to, one or more processors or processing units 1503, a system memory 1512, and a system bus 1513 that couples various system components including the processor 1503 to the system memory 1512.

The system bus 1513 represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus 1513, and all buses specified in this description can also be implemented over a wired or wireless network connection and each of the subsystems, including the processor 1503, a mass storage device 1504, an operating system 1505, application software 1506, data 1507, a network adapter 1508, system memory 1512, an Input/Output Interface 1510, a display adapter 1509, a display device 1511, and a human machine interface 1502, can be contained within one or more remote computing devices 1514*a,b,c* at physically separate locations, connected through buses of this form, in effect implementing a fully distributed system.

The computer 1501 typically includes a variety of computer readable media. Such media can be any available media that is accessible by the computer 1501 and includes both volatile and non-volatile media, removable and non-removable media. The system memory 1512 includes computer readable media in the form of volatile memory, such as random access memory (RAM), and/or non-volatile memory, such as read only memory (ROM). The system memory 1512 typically contains data such as data 1507 and/or program modules such as operating system 1505 and application software 1506 that are immediately accessible to and/or are presently operated on by the processing unit 1503.

The computer 1501 may also include other removable/non-removable, volatile/non-volatile computer storage media. By way of example, FIG. 15 illustrates a mass storage device 1504 which can provide non-volatile storage of computer code, computer readable instructions, data structures, program modules, and other data for the computer 1501. For example, a mass storage device 1504 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device 1504, including by way of example, an operating system 1505 and application software 1506. Each of the operating system 1505 and application software 1506 (or some combination thereof) may include elements of the programming and the application software 1506. Data 1507 can also be stored on the mass storage device 1504. Data 1507 can be stored in any of one or more databases known in the art. Examples of such databases include, DB2®, Microsoft® Access, Microsoft® SQL Server, Oracle®, mySQL, PostgreSQL, and the like. The databases can be centralized or distributed across multiple systems.

A user can enter commands and information into the computer 1501 via an input device (not shown). Examples of such input devices include, but are not limited to, a keyboard, pointing device (e.g., a "mouse"), a microphone, a joystick, a serial port, a scanner, tactile input devices such as gloves, and other body coverings, and the like. These and other input devices can be connected to the processing unit 1503 via a human machine interface 1502 that is coupled to the system bus 1513, but may be connected by other interface and bus structures, such as a parallel port, game port, or a universal serial bus (USB).

A display device 1511 can also be connected to the system bus 1513 via an interface, such as a display adapter 1509. A computer 1501 can have more than one display adapter 1509 and a computer 1501 can have more than one display device 1511. For example, a display device can be a monitor, an LCD (Liquid Crystal Display), or a projector. In addition to the display device 1511, other output peripheral devices can include components such as speakers (not shown) and a printer (not shown) which can be connected to the computer 1501 via Input/Output Interface 1510.

The computer 1501 can operate in a networked environment, using logical connections to one or more remote computing devices 1514*a,b,c*. By way of example, a remote computing device can be a personal computer, portable computer, a server, a router, a network computer, a peer device or other common network node, and so on. Logical connections between the computer 1501 and a remote computing device 1514*a,b,c* can be made via a local area network (LAN) and a general wide area network (WAN). Such network connections can be through a network adapter 1508. A network adapter 1508 can be implemented in both wired and wireless environments. Such networking environments are commonplace in offices, enterprise-wide computer networks, intranets, and the Internet 1515.

One or more VIP displays 1516*a,b,c,d,e* can communicate with the computer 1501. In one aspect, VIP display 1516*e* can communicate with computer 1501 through the input/output interface 1510. This communication can be wired or wireless. Remote VIP displays 1516*a,b,c* can communicate with computer 1501 by communicating first with a respective remote computing device 1514*a,b,c* which then communicates with computer 1501 through the network adapter 1508 via a network such as the Internet 1515. Remote VIP display 1516*d* can communicate with computer 1501 without the need for a remote computing device. Remote VIP display 1516*d* can communicate via a network, such as the Internet 1515. The VIP displays 1516*a,b,c,d,e* can communicate wireless or through a wired connection. The VIP displays 1516*a,b,c,d,e* can communicate individual or collectively as part of a VIP display network.

For purposes of illustration, application programs and other executable program components such as the operating system 1505 are illustrated herein as discrete blocks, although it is recognized that such programs and components reside at various times in different storage components of the computing device 1501, and are executed by the data processor(s) of the computer. An implementation of application software 1506 may be stored on or transmitted across some form of computer readable media. Computer readable media can be any available media that can be accessed by a computer. By way of example, and not limitation, computer readable media may comprise "computer storage media" and "communications media." "Computer storage media" include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the inventive concepts or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made in the present methods and systems without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for role designation comprising:
    rendering a common field of interest via a local device comprising a display that reflects a presence of a plurality of elements, wherein at least one of the elements is a remote element located remotely from another of the elements;
    rendering a graphical user interface comprising a user engageable element indicating a role designation associated with one or more pre-defined, stored parameters;
    receiving a selection of the role designation via the user engageable element of the graphical user interface, wherein the selection of the role designation initiates transmission of a role change request and causes transmission of an indication of a role change to a remote device rendering the common field of interest;
    upon determining the selected role designation associated with the one or more pre-defined, stored parameters, retrieving the stored parameters associated with the selected role designation; and
    updating the common field of interest based upon at least the retrieved stored parameters;
    outputting the updated common field of interest to the display via the graphical user interface, such that merged video presented via the local device has a display characteristic that is distinct from a display characteristic of the merged video presented via the remote device, wherein the display characteristic of the merged video presented via the remote device is dependent upon the selected role designation; and wherein the selected role designation from the local device comprises one of a helper role and an operator role, and wherein the selected role designation from the remote device comprises one of the helper role and the operator role not currently selected by the local device.

2. The method of claim 1, further comprising the step of rendering interaction between the elements in the common field of interest, wherein the rendering of the interactions are controlled based at least upon the retrieved stored parameters.

3. The method of claim 1, wherein each of the elements in the common field of interest is rendered to a remote viewer and a local viewer with a substantially similar alignment and orientation.

4. The method of claim 1, wherein the retrieved stored parameters comprise at least an opacity parameter and further comprising rendering one or more graphical controls configured to control the visual appearance of the common field of interest.

5. The method of claim 1, wherein when the operator role is selected, one or more images captured by the local camera and processed by the local processor are rendered either with a degree of transparency or with substantially full opacity.

6. The method of claim 5, wherein when the operator role is selected, one or more images captured by the remote camera and processed by the remote processor are rendered with a degree of transparency.

7. The method of claim 1, wherein a heads up role designation may be selected via the user engageable element of the graphical user interface, where one or more local images may be rendered in a display screen of the local device, with one or more remote images displayed in a smaller window, or one or more remote images may be rendered in a majority of the display screen of the local viewer, with one or more local images displayed in a smaller window.

8. The method of claim 1, wherein the display characteristic of the merged video presented via the local device is dependent upon the selected role designation.

9. A method for role designation comprising:
generating a first image representing a first element;
generating a second image representing a second element disposed remotely from the first element;
rendering an interface element to one or more of a local user and a remote user relating to a plurality of stored role designations, each of the stored role designations having a set of pre-defined display parameters associated therewith, wherein the interface element is rendered to a local user via a local device comprising a display that reflects a presence of a plurality of elements and at least one of the elements is a remote element located remotely from another of the elements, and
receiving a selection of the interface element representing a selection of a role designation from the plurality of stored role designations, wherein the selection is received from the one or more of the local user and the remote user, wherein the selection of the role designation initiates transmission of a role change request and causes transmission of an indication of the role change request to a remote device rendering a common field of interest;
upon determining the selected role designation having a set of pre-defined display parameters, retrieving the parameters associated with the selected role designation;
updating the interface element based upon at least the retrieved pre-defined display parameters;
generating, in response to the role change request, a composite image including the first image and the second image;
outputting the composite image to the display,
wherein a display characteristic of at least one of the first image and the second image relative to the other of the first image and the second image is modified based upon the set of pre-defined display parameters associated with the selected role designation,
wherein the composite image presented via the local device has a display characteristic that is distinct from a display characteristic of the composite image presented via the remote device, wherein the display characteristic of the composite image presented via the remote device is dependent upon the selected role designation; and
wherein the selected role designation from the local user comprises one of a helper role and an operator role, and wherein the selected role designation from the remote user comprises one of the helper role and the operator role not currently selected by the local user.

10. The method according to claim 9, wherein the display characteristic is opacity.

11. The method according to claim 9, wherein the display characteristic is an orientation or arrangement of the one or more of the first element and the second element.

12. The method according to claim 9, wherein the method further comprises outputting the composite image to a remote display,
wherein the remote display reflects a presence of a plurality of elements and at least one of the elements is a remote element located remotely from another of the elements,
wherein the display characteristic of the composite image presented via the remote device is dependent upon the selected role designation, and
wherein one or more of the first element and the second element is a representation of the physical presence of one or more of the remote user and the local user.

13. The method of claim 9, wherein at least one of the first image and the second image is part of a video stream.

14. The method of claim 9, wherein at least one of the first image and the second image is part of a live video stream.

15. The method of claim 9, wherein a heads up role designation may be selected via the interface element, where one or more local images may be rendered in a display screen of the local user, with one or more remote images displayed in a smaller window, or one or more remote images may be rendered in a majority of the display screen of the local user, with one or more local images displayed in a smaller window.

16. A system for role designation comprising:
a display configured for displaying a common field of interest;
a sensor configured for obtaining image data;
a processor in signal communication with the display and the sensor,
wherein the processor is configured to perform steps comprising, rendering the common field of interest via a local device that reflects a presence of a plurality of elements, wherein at least one of the elements is a remote element located remotely from another of the elements;

rendering a graphical user interface comprising a user engageable element indicating a role designation associated with one or more pre-defined, stored parameters;

receiving a selection of the role designation via the user engageable element of the graphical user interface, wherein the selection of the role designation initiates transmission of a role change request and causes transmission of an indication of a role change to a remote device rendering the common field of interest;

upon determining the selected role designation associated with one or more pre-defined, stored parameters, retrieving stored parameters associated with the selected role designation;

updating the common field of interest based upon at least the retrieved stored parameters such that merged video presented via the local device has a display characteristic that is distinct from a display characteristic of merged video presented via the remote device, wherein the display characteristic of the merged video presented via the remote device is dependent upon the selected role designation; and outputting the updated common field of interest to the display via the graphical user interface, wherein the selected role designation from the local device comprises one of a helper role and an operator role, and wherein the selected role designation from the remote device comprises one of the helper role and the operator role not currently selected by the local device.

17. The system of claim 16, wherein the sensor is at least one of a camera, an infrared sensor, a light sensor, a RADAR device, a SONAR device, a computed tomography device, a magnetic resonance imaging device, and a depth scan sensor.

18. The system of claim 16, wherein the processor is further configured to continuously update the common field of interest such that the presence of the remote element is rendered in real time to a local viewer.

19. The system of claim 16, wherein the processor is further configured to continuously update the common field of interest such that the presence of a local one of the elements is rendered in real time to a remote viewer.

20. The method of claim 16, wherein a heads up role designation may be selected via the user engageable button of the graphical user interface, where one or more local images may be rendered in a display screen of the local device, with one or more remote images displayed in a smaller window, or one or more remote images may be rendered in a majority of the display screen of the local device, with one or more local images displayed in a smaller window.

* * * * *